US007981437B2

(12) United States Patent
Kordes et al.

(10) Patent No.: US 7,981,437 B2
(45) Date of Patent: Jul. 19, 2011

(54) INDANYL- AND TETRAHYDRONAPHTHYL-AMINO-AZOLINE COMPOUNDS FOR COMBATING ANIMAL PESTS

(75) Inventors: Markus Kordes, Frankenthal (DE); Christopher Koradin, Ludwigshafen (DE); Deborah L. Culbertson, Fuquay Varina, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/094,854

(22) PCT Filed: Nov. 15, 2006

(86) PCT No.: PCT/EP2006/068482
§ 371 (c)(1),
(2), (4) Date: May 23, 2008

(87) PCT Pub. No.: WO2007/060121
PCT Pub. Date: May 31, 2007

(65) Prior Publication Data
US 2008/0293569 A1 Nov. 27, 2008

Related U.S. Application Data

(60) Provisional application No. 60/739,730, filed on Nov. 25, 2005.

(51) Int. Cl.
*A61K 31/4168* (2006.01)
*A61K 31/42* (2006.01)
*A61K 31/426* (2006.01)
*A01N 43/50* (2006.01)
*A01N 43/76* (2006.01)
*A01N 43/78* (2006.01)
*C07D 277/04* (2006.01)
*C07D 277/18* (2006.01)
*C07D 233/02* (2006.01)
*C07D 233/50* (2006.01)
*C07D 263/04* (2006.01)
*C07D 263/28* (2006.01)

(52) U.S. Cl. ........ 424/405; 514/370; 514/377; 514/385; 548/190; 548/234; 548/331.5

(58) Field of Classification Search ........................ None
See application file for complete search history.

(56) References Cited

U.S. PATENT DOCUMENTS

| 2,870,161 | A | * | 1/1959 | Bloom | 548/234 |
| 3,636,219 | A | * | 1/1972 | Culik et al. | 514/291 |
| 3,679,798 | A | * | 7/1972 | Culik et al. | 514/304 |
| 4,575,501 | A | | 3/1986 | Behner et al. | |
| 2008/0300285 | A1 | * | 12/2008 | O'Sullivan et al. | 514/370 |

FOREIGN PATENT DOCUMENTS

| DE | 1 963 192 | | 6/1971 |
| EP | 0 073 393 | | 3/1983 |
| WO | WO 89/09542 | | 10/1989 |
| WO | WO 2007/020377 | | 2/2007 |
| WO | WO 2007/093292 | * | 8/2007 |
| WO | WO 2008/017816 | * | 2/2008 |
| WO | WO 2008/125230 | * | 10/2008 |

OTHER PUBLICATIONS

Lange et al. "The Action of Phenyliminoimidazolidines and 2-Aminooxazoline on Octopamine Receptors on Locust Fat Body", Pesticide Biochemistry and Physiology, 37, 24-29, 1990.*
International Search Report completed Mar. 26, 2007, in corresponding International Application No. PCT/EP2006/068482, filed Nov. 15, 2006.
International Preliminary Examination Report completed Feb. 1, 2008, in corresponding International Application No. PCT/EP2006/068482, filed Nov. 15, 2006.

* cited by examiner

*Primary Examiner* — Yong Chu
*Assistant Examiner* — Michael Barker
(74) *Attorney, Agent, or Firm* — Brinks Hofer Gilson & Lione

(57) ABSTRACT

The present invention relates to Indanyl- and Tetrahydronaphthyl-amino-azoline compounds of formula I

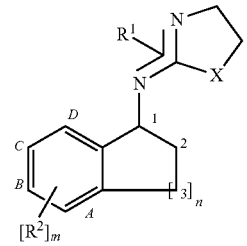

formula I wherein the variables $R^1$ and $R^2$ are as defined in description.

The invention relates also to methods of combating or controlling insects, arachnids or nematodes, to methods for protecting growing plants from attack or infestation by insects, arachnids or nematodes, to methods for the protection of seeds from soil insects and of the seedlings' roots and shoots from soil and foliar insects and to methods for treating, controlling, preventing or protecting animals against infestation or infection by parasites.

28 Claims, No Drawings

INDANYL- AND TETRAHYDRONAPHTHYL-AMINO-AZOLINE COMPOUNDS FOR COMBATING ANIMAL PESTS

This application is a National Stage application of International Application No. PCT/EP2006/068482, filed Nov. 15, 2006, which claims the benefit of U.S. Provisional Application No. 60/739,730, filed Nov. 25, 2005, the entire contents of which is hereby incorporated herein by reference.

The present invention relates to Indanyl- or Tetrahydronaphthyl-amino-azoline compounds, which are useful for combating animal pests. The present invention also relates to methods for combating animal pests and to agricultural compositions for combating animal pests.

Animal pests and in particular insects, arachnids and nematodes destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating insects, arachnids and nematodes.

Compounds similar to those of formula I have been described in DE-A1963192.

However, these compounds described in DE-A1963192 are limited in their activity or with regard to the broadness of their activity spectrum.

It is therefore an object of the present invention to provide compounds having a good pesticidal activity and showing a broad activity spectrum against a large number of different animal pests, especially against difficult to control insects, arachnids and nematodes.

It has been found that these objectives can be achieved by Indanyl- or Tetrahydronaphthyl-amino-azoline compounds of the formula I:

formula I

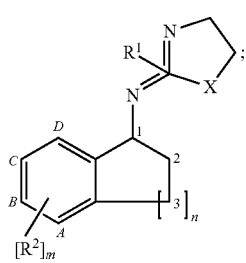

which are also represented by the following two isomeric formulas:

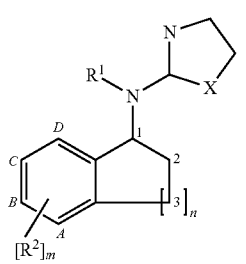

or

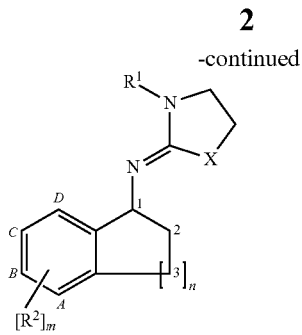

and wherein n is 1 or 2;

m is 1, 2, 3 or 4, wherein when that m is greater than 1, the radicals $R^2$ may have the same or different meanings X is O, S, $NR^3$, wherein $R^3$ is selected from hydrogen, cyano, nitro, formyl, $C(=O)R^{3c}$, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy $C_2$-$C_6$-alkynylamino, di($C_2$-$C_6$-alkynyl)amino, ($C_1$-$C_6$-alkoxy)methylen, $C_1$-$C_6$-alkylsulfinyl, $C_1$-$C_6$-alkylsulfenyl or $C_1$-$C_6$-alkylsulfonyl wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, or $C(O)NR^{3a}R^{3b}$, $(SO_2)NR^{3a}R^{3b}$, phenyl, phenyloxy or benzyl, each of the last three mentioned radicals may be unsubstituted or substituted with 1 to 5 radicals, independently of one another selected from the group consisting of halogen, $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy and $C_1$-$C_6$-haloalkoxy radicals; and wherein $R^{3a}$ and $R^{3b}$ are each independently selected from hydrogen, $C_1$-$C_6$-alkyl, $C_1$-$C_6$-haloalkyl, $C_2$-$C_6$-alkenyl, or $C_2$-$C_6$-alkynyl.

$R^{3c}$ is selected from hydrogen, $C_1$-$C_6$-alkyl, $C_2$-$C_6$-alkenyl, $C_2$-$C_6$-alkinyl, $C_3$-$C_8$-cycloalkyl, $C_1$-$C_6$-alkylthio, $C_1$-$C_6$-alkoxy, ($C_1$-$C_6$-alkyl)amino, di($C_1$-$C_6$-alkyl)amino, phenyl and heteroaryl, which can be a mono- or bicyclic 5 to 10 membered heteroaromatic ring, which contains 1, 2, 3 or 4 heteroatoms selected from O, S and N $R^1$ is selected from hydrogen, cyano, nitro, formyl, $C(=O)R^{1c}$, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, ($C_1$-$C_6$-alkoxy) methylen, $C_1$-$C_6$-alkylsulfinyl, $C_1$-$C_6$-alkylsulfenyl or $C_1$-$C_6$-alkylsulfonyl wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_1$-$C_6$-alkynyloxy, $C_1$-$C_6$-haloalkoxy and $C_1$-$C_6$-alkylthio, or $C(O)NR^{1a}R^{1b}$, $(SO_2)NR^{1a}R^{1b}$, phenyl, phenyloxy or benzyl, each of the last three mentioned radicals may be unsubstituted or substituted with 1 to 5 radicals, independently of one another selected from the group consisting of halogen, $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy and $C_1$-$C_6$-haloalkoxy; and wherein $R^{1a}$ and $R^{1b}$ are each independently selected from hydrogen, $C_1$-$C_6$-alkyl, $C_1$-$C_6$-haloalkyl, $C_2$-$C_6$-alkenyl, or $C_2$-$C_6$-alkynyl.

$R^{1c}$ is selected from hydrogen, $C_1$-$C_6$-alkyl, $C_2$-$C_6$-alkenyl, $C_2$-$C_6$-alkinyl, $C_3$-$C_8$-cycloalkyl, $C_1$-$C_6$-alkylthio, $C_1$-$C_6$-alkoxy, ($C_1$-$C_6$-alkyl)amino, di($C_1$-$C_6$-alkyl)amino, phenyl and heteroaryl, which can be a mono- or bicyclic 5 to 10 membered heteroaromatic ring, which contains 1, 2, 3 or 4 heteroatoms selected from O, S and N $R^2$ is selected from halogen, OH, SH, $NH_2$, $SO_3H$, COOH, cyano, azido, nitro, formyl, $CONH_2$, $CSNH_2$, CH=N—OH, CH=N—O—($C_1$-$C_6$)-alkyl, C(=O)$R^{2c}$, C(=S)$R^{2c}$, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, $C_1$-$C_6$-alkylamino, di($C_1$-$C_6$-alkyl)amino, $C_1$-$C_8$-alkylthio, $C_2$-$C_6$-alkenyl, $C_2$-$C_6$-alkenyloxy, $C_2$-$C_6$-alkenylamino, $C_2$-$C_6$-alkenylthio, $C_2$-$C_6$-alkynyl, $C_2$-$C_6$-alkynyloxy, $C_2$-$C_6$-alkynylamino, $C_2$-$C_6$-alkynylthio, $C_1$-$C_6$-alkylsulfonyl, $C_1$-$C_6$-alkylsulfoxyl, $C_2$-$C_6$-alkenylsulfonyl, $C_2$-$C_6$-alkynylsulfonyl, ($C_1$-$C_6$-alkoxy)carbonyl, ($C_2$-$C_6$-alkenyloxy)carbonyl, ($C_2$-$C_6$-alkynyloxy)-carbonyl, ($C_1$-$C_6$-alkyl)carbonyloxy, ($C_2$-$C_6$-alkenyl-)carbonyloxy or ($C_2$-$C_6$-alkynyl-)carbonyloxy, ($C_2$-$C_6$-alkenyl)carbonylamino, wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio; $C(O)NR^{2a}R^{2b}$, $(SO_2)NR^{2a}R^{2b}$, wherein $R^{2a}$ and $R^{2b}$ are each independently selected from hydrogen, OH, $NH_2$, $C_1$-$C_6$-alkyl, $C_1$-$C_6$-haloalkyl, $C_2$-$C_6$-alkenyl or $C_2$-$C_6$-alkynyl.

$R^{2c}$ is selected from hydrogen, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, ($C_1$-$C_6$-alkyl)amino, di($C_1$-$C_6$-alkyl)amino, hydrazino, ($C_1$-$C_6$-alkyl)hydrazino, di($C_1$-$C_6$-alkyl)hydrazino, phenyl and heteroaryl, which can be a mono- or bicyclic 5 to 10 membered heteroaromatic ring, which contains 1, 2, 3 or 4 heteroatoms selected from O, S and N;

a radical Y—Ar or a radical Y-Cy, wherein

Y is a single bond, oxygen, sulfur, nitrogen, $C_1$-$C_6$-alkandiyl or $C_1$-$C_6$-alkandiyloxy;

Ar is phenyl, naphthyl or a mono- or bicyclic 5- to 10-membered heteroaromatic ring, which contains 1, 2, 3 or 4 heteroatoms selected from 2 oxygen, 2 sulfur and 3 nitrogen atoms as ring members, wherein Ar is unsubstituted or may carry any combination of 1 to 5 radicals, independently of one another selected from the group consisting of halogen, cyano, nitro, hydroxy, mercapto, amino, carboxyl, $C_1$-$C_6$-alkyl, $C_1$-$C_6$-haloalkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

Cy is $C_3$-$C_{12}$-cycloalkyl, which is unsubstituted or substituted with 1 to 5 radicals, independently of one another selected from the group consisting of halogen, cyano, nitro, hydroxy, mercapto, amino, carboxyl, $C_1$-$C_6$-alkyl, $C_1$-$C_6$-haloalkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

and wherein the radical $R^2$ that are bound to adjacent carbon atoms of the phenyl rings may form, together with said carbon atoms, a fused benzene ring, a fused saturated or partially unsaturated 5-, 6-, or 7-membered carbocycle or a fused 5-, 6- or 7-membered heterocycle, which contains 1, 2, 3 or 4 heteroatoms selected from two oxygen, two sulfur and three nitrogen atoms as ring members, and wherein the fused ring is unsubstituted or may carry 1, 2, 3 or 4 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

or the enantiomers and/or the agriculturally and/or veterinary acceptable salts thereof;

with the proviso that compound of formula I is not 2-(4-thio-tert-butyl-1-indanylamino)-oxazoline.

Therefore, the present invention relates to Indanyl- or Tetrahydronaphthyl-amino-azoline compounds of the formula I, or their enantiomers and to the agriculturally or veterinary acceptable salts thereof. These compounds have a high pesticidal activity and are active against a broad spectrum of animal pests, especially against insects, arachnids and nematodes.

The invention also relates to a method of combating animal pests, especially insects, arachnids and nematodes, which comprises contacting the animal pests, their habit, breeding ground, food supply, plant, seed, soil, area, material or environment in which the animal pests are growing or may grow, or the materials, plants, seeds, soils, surfaces or spaces to be protected from 1 attack or infestation by the animal pests, especially insects, arachnids or nematodes, with a pesticidally effective amount of at least one Indanyl- or Tetrahydronaphthyl-amino-azoline compound of the formula I and/or at least one agriculturally acceptable salt thereof.

Furthermore, the present invention provides a method for protecting crops from attack or infestation by animal pests, especially insects, arachnids or nematodes, which comprises contacting a crop with a pesticidally effective amount of at least one Indanyl- or Tetrahydronaphthyl-amino-azoline compound of the formula I and/or at least one salt thereof.

Furthermore, the invention relates to agricultural compositions, preferably in the form of directly sprayable solutions, emulsions, pastes oil dispersions, powders, materials for scattering, dusts or in the form of granules, which comprise at least one Indanyl- or Tetrahydronaphthyl-amino-azoline compound of the formula I as defined above or a salt thereof, admixed with one or more agronomically acceptable inert, solid or liquid carrier(s) and, if desired, at least one surfactant.

Indanyl- or Tetrahydronaphthyl-amino-azoline have been described for pharmacological use in conventional art.

Wong, W. C. et al discloses a convenient synthesis of 2-amino-2-oxazolines and their pharmacological evaluation at cloned human alpha-adrenergic receptors (Bioorg. & Med. Chem. Lett, 4(19), 1994, p. 1217-22).

The hydrolytic degradation of oxamethazoline compounds is discussed by Yamana, T. et al. (Yakuzaiguku (1967), 27(3). P. 203-5)

In U.S. Pat. No. 3,296,077 the presence of 2-(1-tetrahydronaphthyl amino)-imidazolines compounds can be found in shaving compositions. 2-(1-Tetrahydronaphthyl amino)-imidazoline compounds are also described for their sympathomimetic effects in Nippon Yakurigaku Zasshi (1965), 61(6), p. 479-89 for their vasoconstrictor effects in U.S. Pat.

No. 4,520,014 or for their efficiency in nasal compositions in Arzneimittelforschung 1962, 12, p. 975-8.

U.S. Pat. No. 2,883,410, U.S. Pat. No. 2,870,161 and U.S. Pat. No. 2,870,159 describe 2-(1-indanyl amino)-oxazolines as tranquilizing agents in pharmaceutical compositions, wherein first both discloses 2-(4-thio-tert-butyl-1-indanylamino)-oxazoline. U.S. Pat. No. 2,956,072 discloses 2-(1-Tetrahydronaphthyl amino)-oxazolines for the same purpose.

2-(1-tetrahydronaphthyl amino)-derivatives or 2-(1-indanyl amino)-derivatives having a thiazoline, oxazoline or imidazoline substitution can be found in U.S. Pat. No. 3,636,219 and U.S. Pat. No. 3,679,798, where there are described for their anticholinergic effect.

Aryl-amino-oxazolines or aryl-amino-thiazolines have been discussed as pesticides in DE-A 1 963 192 or for crop protection in DE-B 1 954 584.

None of the latter two documents discloses derivatives, which reveal indanyl- or tetrahydronaphthyl-amino-azolines having a comparable substitution scheme, wherein the aromatic part of the indanyl or tetrahydronapthyl ring system is substitued. Preferably the indanyl- or tetrahydronaphthyl-amino-azoline is substituted at positions A and/or C and/or D. Preferably the uncondensed part of the indanyl or tetrahydronaphthyl ring system remains unsubstituted as well as the azoline ring remains unsubstituted.

The compounds of the formula I may have one or more centers of chirality, in which case they are present as mixtures of stereoisomers, such as enantiomers or diastereomers. The present invention provides both the pure stereoisomers, e.g. the pure enantiomes or diastereomers, and mixtures thereof. The compounds of the formula I may also exist in the form of different tautomers. The invention comprises the single tautomers, if seperable, as well as the tautomer mixtures.

Salts of the compounds of the formula I which are suitable for the use according to the invention are especially agriculturally acceptable salts. They can be formed in a customary method, e.g. by reacting the compound with an acid of the anion in question if the compound of formula I has a basic functionality or by reacting an acidic compound of formula I with a suitable base.

Suitable agriculturally useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl and/or benzyl.

Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

Examples of other meanings are:

The term "$C_1$-$C_6$-alkyl" as used herein and in the alkyl moieties of $C_1$-$C_6$-alkoxy, $C_1$-$C_6$-alkylamino, di($C_1$-$C_6$-alkyl)amino, $C_1$-$C_6$-alkylthio, $C_1$-$C_6$-alkylsulfonyl, $C_1$-$C_6$-alkylsulfoxyl, $C_1$-$C_6$-alkylcarbonyl, $C_1$-$C_6$-alkoxycarbonyl, $C_1$-$C_6$-alkylthiocarbonyl, and $C_1$-$C_6$-alkylcarbonyloxy refer to a saturated straight-chain or branched hydrocarbon group having 1 to 6 carbon atoms, especially 1 to 4 carbon groups, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_1$-$C_6$-haloalkyl" as used herein refers to a straight-chain or branched saturated alkyl group having 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term, "$C_1$-$C_6$-alkoxy" as used herein refers to a straight-chain or branched saturated alkyl group having 1 to 6 carbon atoms (as mentioned above) which is attached via an oxygen atom. Examples include $C_1$-$C_6$-alkoxy such as methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethyl propoxy, n-hexoxy, 1-methylpentoxy, 2-methylpentoxy, 3-methylpentoxy, 4-methylpentoxy, 1,1-dimethyl butoxy, 1,2-dimethyl butoxy, 1,3-dimethyl butoxy, 2,2-dimethyl butoxy, 2,3-dimethyl butoxy, 3,3-dimethylbutoxy, 1-ethyl butoxy, 2-ethyl butoxy, 1,1,2-trimethylpropoxy, 1,2,2-trimethylpropoxy, 1-ethyl-1-methylpropoxy, 1-ethyl-2-methylpropoxy and the like.

The term "$C_1$-$C_6$-haloalkoxy" as used herein refers to a $C_1$-$C_6$-alkoxy group as mentioned above wherein the hydrogen atoms are partially or fully substituted by fluorine, chlorine, bromine and/or iodine, i.e., for example, $C_1$-$C_6$-haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, in particular chloromethoxy, fluoromethoxy, difluoromethoxy, trifluoromethoxy, 2-fluoroethoxy, 2-chloroethoxy or 2,2,2-trifluoroethoxy.

The term "$C_1$-$C_6$-alkoxy-$C_1$-$C_6$-alkyl" as used herein refers to $C_1$-$C_6$-alkyl wherein 1 carbon atom carries a $C_1$-$C_6$-alkoxy radical as mentioned above. Examples are $CH_2$—$OCH_3$, $CH_2$—$OC_2H_5$, n-propoxymethyl, $CH_2$—OCH($CH_3$)$_2$, n-butoxymethyl, (1-methylpropoxy)methyl, (2-methylpropoxy)methyl, $CH_2$—OC($CH_3$)$_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl and the like.

The term "($C_1$-$C_6$-alkyl)carbonyl" as used herein refers to a straight-chain or branched saturated alkyl group having 1 to 6 carbon atoms (as mentioned above) bonded via the carbon atom of the carbonyl group at any bond in the alkyl group. Examples include $C_1$-$C_6$-alkylcarbonyl such CO—$CH_3$, CO—$C_2H_5$, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethyl propylcarbonyl, 1-ethyl-1-methylpropylcarbonyl or 1-ethyl-2-methylpropylcarbonyl and the like.

The term "($C_1$-$C_6$-alkoxy)carbonyl" as used herein refers to a straight-chain or branched alkoxy group (as mentioned above) having 1 to 6 carbon atoms attached via the carbon atom of the carbonyl group, for example CO—$OCH_3$, CO—$OC_2H_5$, COO—$CH_2$—$C_2H_5$, CO—OCH($CH_3$)$_2$, n-butoxycarbonyl, CO—OCH($CH_3$)—$C_2H_5$, CO—$OCH_2$—CH($CH_3$)$_2$, CO—OC($CH_3$)$_3$, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methyl pentoxycarbonyl, 1,1-dimethyl butoxycarbonyl, 1,2-dimethyl butoxycarbonyl, 1,3-dimethylbutoxycarbonyl, 2,2-dimethyl butoxycarbonyl, 2,3-dimethyl butoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethyl propoxycarbonyl, 1-ethyl-1-methylpropoxycarbonyl or 1-ethyl-2-methylpropoxycarbonyl.

The term "($C_1$-$C_6$-alkyl)carbonyloxy" as used herein refers to a straight-chain or branched saturated alkyl group having 1 to 6 carbon atoms (as mentioned above) bonded via the carbon atom of the carbonyloxy group at any bond in the alkyl group, for example O—CO—$CH_3$, O—CO—$C_2H_5$, n-propylcarbonyloxy, 1-methylethylcarbonyloxy, n-butylcarbonyloxy, 1-methylpropylcarbonyloxy, 2-methylpropylcarbonyloxy, 1,1-dimethylethylcarbonyloxy, n-pentylcarbonyloxy, 1-methylbutylcarbonyloxy, 2-methylbutylcarbonyloxy, 3-methylbutylcarbonyloxy, 1,1-dimethylpropylcarbonyloxy or 1,2-dimethylpropylcarbonyloxy.

The term "$C_1$-$C_6$-alkylthio ($C_1$-$C_6$-alkylsulfanyl: $C_1$-$C_6$-alkyl-S—)" as used herein refers to a straight-chain or branched saturated alkyl group having 1 to 6 carbon atoms (as mentioned above) which is attached via a sulfur atom, for example $C_1$-$C_4$-alkylthio such as methylthio, ethylthio, propylthio, 1-methylethylthio, butylthio, 1-methylpropylthio, 2-methylpropylthio, 1,1-dimethylethylthio, n-pentylthiocarbonyl, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethyl propylthio, 1-ethyl-1-methylpropylthio or 1-ethyl-2-methylpropylthio.

The term "($C_1$-$C_6$-alkylthio)carbonyl" as used herein refers to a straight-chain or branched alkthio group (as mentioned above) having 1 to 6 carbon atoms attached via the carbon atom of the carbonyl group. Examples include CO—$SCH_3$, CO—$SC_2H_5$, CO—$SCH_2$—$C_2H_5$, CO—SCH($CH_3$)$_2$, n-butylthiocarbonyl, CO—SCH($CH_3$)—$C_2H_5$, CO—$SCH_2$—CH($CH_3$)$_2$, CO—SC($CH_3$)$_3$, n-pentylthiocarbonyl, 1-methylbutylthiocarbonyl, 2-methylbutylthiocarbonyl, 3-methylbutylthiocarbonyl, 2,2-dimethylpropylthiocarbonyl, 1-ethylpropylthiocarbonyl, n-hexylthiocarbonyl, 1,1-dimethylpropylthiocarbonyl, 1,2-dimethylpropylthiocarbonyl, 1-methylpentylthiocarbonyl, 2-methylpentylthiocarbonyl, 3-methylpentylthiocarbonyl, 4-methylpentylthiocarbonyl, 1,1-dimethylbutylthiocarbonyl, 1,2-dimethylbutylthiocarbonyl, 1,3-dimethylbutylhiocarbonyl, 2,2-dimethylbutylthiocarbonyl, 2,3-dimethylbutylthiocarbonyl, 3,3-dimethylbutylthiocarbonyl, 1-ethylbutlthioycarbonyl, 2-ethylbutylthiocarbonyl, 1,1,2- trimethylpropylthiocarbonyl, 1,2,2-trimethylpropylthiocarbonyl, 1-ethyl-1-methylpropylthiocarbonyl or 1-ethyl-2-methylpropylthiocarbonyl.

The term "$C_1$-$C_6$-alkylsulfinyl" ($C_1$-$C_6$-alkylsulfoxyl: $C_1$-$C_6$-alkyl-S(=O)—), as used herein refers to a straight-chain or branched saturated hydrocarbon group (as mentioned above) having 1 to 6 carbon atoms bonded through the sulfur atom of the sulfinyl group at any bond in the alkyl group, for example SO—$CH_3$, SO—$C_2H_5$, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethyl butylsulfinyl, 2-ethyl butylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

The term "$C_1$-$C_6$-alkylamino" refers to a secondary amino group carrying one alkyl group as defined above, e.g. methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino.

The term "di($C_1$-$C_6$-alkyl)amino" refers to a tertiary amino group carrying two alkyl radicals as defined above, e.g. dimethylamino, diethylamino, di-n-propylamino, diisopropylamino, N-ethyl-N-methylamino, N-(n-propyl)-N-methylamino, N-(isopropyl)-N-methylamino, N-(n-butyl)-N-methylamino, N-(n-pentyl)-N-methylamino, N-(2-butyl)-N-methylamino, N-(isobutyl)-N-methylamino, N-(n-pentyl)-N-methylamino, N-(n-propyl)-N-ethylamino, N-(isopropyl)-N-ethylamino, N-(n-butyl)-N-ethylamino, N-(n-pentyl)-N-ethylamino, N-(2-butyl)-N-ethylamino, N-(isobutyl)-N-ethylamino or N-(n-pentyl)-N-ethylamino.

The term "$C_1$-$C_6$-alkylsulfonyl" ($C_1$-$C_6$-alkyl-S(=O)$_2$—) as used herein refers to a straight-chain or branched saturated alkyl group having 1 to 6 carbon atoms (as mentioned above) which is bonded via the sulfur atom of the sulfonyl group at any bond in the alkyl group, for example $SO_2$—$CH_3$, $SO_2$—$C_2H_5$, n-propylsulfonyl, $SO_2$—CH($CH_3$)$_2$, n-butylsulfonyl, 1-methylpropylsulfonyl, 2-methylpropylsulfonyl, $SO_2$—C($CH_3$)$_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl.

The term "$C_2$-$C_6$-alkenyl" as used herein and in the alkenyl moieties of $C_2$-$C_6$-alkenyloxy, $C_2$-$C_6$-alkenylamino, $C_2$-$C_6$-alkenylthio, $C_2$-$C_6$-alkenylsulfonyl, ($C_2$-$C_6$-alkenyl)carbonyl, ($C_2$-$C_6$-alkenyloxy)carbonyl and ($C_2$-$C_6$-alkenyl)carbonyloxy refers to a straight-chain or branched unsaturated hydrocarbon group having 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term, "$C_2$-$C_6$-alkenyloxy" as used herein refers to a straight-chain or branched saturated alkenyl group having 2 to 6 carbon atoms (as mentioned above) which is attached via an oxygen atom, such as vinyloxy, allyloxy (propen-3-yloxy), methallyloxy, buten-4-yloxy, etc.

The term "$C_2$-$C_6$-alkenylthio" as used herein refers to a straight-chain or branched saturated alkenyl group having 2 to 6 carbon atoms (as mentioned above) which is attached via a sulfur atom, for example vinylsulfanyl, allylsulfanyl (propen-3-ylthio), methallylsufanyl, buten-4-ylsulfanyl, etc.

The term "$C_2$-$C_6$-alkenylamino" as used herein refers to a straight-chain or branched saturated alkenyl group having 2 to 6 carbon atoms (as mentioned above) which is attached via a sulfur atom, for example vinylamino, allylamino (propen-3-ylamino), methallylamino, buten-4-ylamino, etc.

The term "$C_2$-$C_6$-alkenylsulfonyl" as used herein refers to a straight-chain or branched saturated alkenyl group having 2 to 6 carbon atoms (as mentioned above) which is attached via a sulfonyl ($SO_2$) group, for example vinylsulfonyl, allylsulfonyl (propen-3-ylsulfonyl), methallylsulfonyl, buten-4-ylsulfonyl, etc.

The term "$C_2$-$C_6$-alkynyl" as used herein and in the alkynyl moieties of $C_2$-$C_6$-alkynyloxy, $C_2$-$C_6$-alkynylamino, $C_2$-$C_6$-alkynylthio, $C_2$-$C_6$-alkynylsulfonyl, $C_2$-$C_6$-alkynylcarbonyl, $C_2$-$C_6$-alkynyloxycarbonyl and $C_1$-$C_6$-alkynylcarbonyloxy refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn- 4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methyl pent-1-yn-1-yl, 3-methyl pent-1-yn-3-yl, 3-methyl pent-1-yn-4-yl, 3-methyl pent-1-yn-5-yl, 4-methyl pent-1-yn-1-yl, 4-methyl pent-2-yn-4-yl or 4-methyl pent-2-yn-5-yl and the like.

The term, "$C_2$-$C_6$-alkynyloxy" as used herein refers to a straight-chain or branched saturated alkynyl group having 2 to 6 carbon atoms (as mentioned above) which is attached via an oxygen atom, such as propargyloxy (propin-3-yloxy), butin-3-yloxy, and butin-4-yloxy.

The term "$C_2$-$C_6$-alkynylthio" as used herein refers to a straight-chain or branched saturated alkynyl group having 2 to 6 carbon atoms (as mentioned above) which is attached via a sulfur atom, such as propargylsulfanyl (propin-3-ylthio), butin-3-ylsufanyl and butin-4-ylsulfanyl.

The term "$C_2$-$C_6$-alkynylamino" as used herein refers to a straight-chain or branched saturated alkynyl group having 2 to 6 carbon atoms (as mentioned above) which is attached via a sulfur atom, such as propargylamino (propin-3-ylamino), butin-3-amino, and butin-4-ylamino.

The term "$C_2$-$C_6$-alkynylsulfonyl" as used herein refers to a straight-chain or branched saturated alkynyl group having 2 to 6 carbon atoms (as mentioned above) which is attached via a sulfonyl ($SO_2$) group, such as propargylsulfonyl (propin-3-ylsulfonyl), butin-3-ylsulfonyl and butin-4-ylsulfonyl.

The term "$C_3$-$C_{12}$-cycloalkyl" as used herein refers to a mono- or bi- or polycyclic hydrocarbon radical having 3 to 12 carbon atoms, in particular 3 to 6 carbon atoms. Examples of monocyclic radicals comprise cyclopropyl, cyclobutyl, cyclopentyl, cyclohexyl, cycloheptyl, cyclooctyl, cyclononyl and cyclodecyl. Examples of bicyclic radicals comprise bicyclo[2.2.1]heptyl, bicyclo[3.1.1]heptyl, bicyclo[2.2.2]octyl and bicyclo[3.2.1]nonyl. Examples of tricylcic radicals are adamantyl and homoadamantyl.

The term "mono- or bicylcic heteroaromatic ring" as used herein refers to a monocyclic heteroaromatic radical which has 5 or 6 ring members, which may comprise a fused 5, 6 or 7 membered ring thus having a total number of ring members from 8 to 10, wherein in each case 1, 2, 3 or 4 of these ring members are heteroatoms selected, independently from each other, from the group consisting of oxygen, nitrogen and sulfur. The heterocyclic radical may be attached to the remainder of the molecule via a carbon ring member or via a nitrogen ring member. The fused ring comprises $C_5$-$C_7$-cycloalkyl, $C_5$-$C_7$-cycloalkenyl, or 5 to 7 membered heterocyclyl and phenyl.

Examples for monocyclic 5- to 6-membered heteroaromatic rings include triazinyl, pyrazinyl, pyrimidyl, pyridazinyl, pyridyl, thienyl, furyl, pyrrolyl, pyrazolyl, imidazolyl, triazolyl, tetrazolyl, thiazolyl, oxazolyl, thiadiazolyl, oxadiazolyl, isothiazolyl and isoxazolyl.

Examples for 5- to 6-membered heteroaromatic rings carrying a fused phenyl ring are quinolinyl, isoquinolinyl, indolyl, indolizinyl, isoindolyl, indazolyl, benzofuryl, benzthienyl, benzo[b]thiazolyl, benzoxazolyl, benzthiazolyl, benzoxazolyl, and benzimidazolyl. Examples for 5- to 6-membered heteroaromatic rings carrying a fused cycloalkenyl ring are dihydroindolyl, dihydroindolizinyl, dihydroisoindolyl, dihydrochinolinyl, dihydroisochinolinyl, chromenyl, chromanyl and the like.

The term "5 to 7 membered heterocyclyl" comprises monocyclic heteroaromatic rings as defined above and non-aromatic saturated or partially unsaturated heterocyclic rings having 5, 6 or 7 ring members. Examples for non-aromatic rings include pyrrolidinyl, pyrazolinyl, imidazolinyl, pyrrolinyl, pyrazolinyl, imidazolinyl, tetrahydrofuranyl, dihydrofuranyl, 1,3-dioxolanyl, dioxolenyl, thiolanyl, dihydrothienyl, oxazolidinyl, isoxazolidinyl, oxazolinyl, isoxazolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, dioxanyl, thiopyranyl, dihydrothiopyranyl, tetrahydrothiopyranyl, morpholinyl, thiazinyl and the like.

As regards the pesticidal activity of the compounds of formula I, preference is given to those compounds of formula I, in which the variables—independently of one another or in combination with any of the other variables—have the following meanings:

An Indanyl- or Tetrahydronaphthyl-amino-azoline compound of formula I, wherein $R^1$ is selected from hydrogen, cyano, C(=O)$R^{1c}$, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, and wherein $R^{1c}$ is selected from hydrogen, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, ($C_1$-$C_6$-alkyl)amino, di($C_1$-$C_6$-alkyl)amino, phenyl and heteroaryl, which can be a mono- or bicyclic 5 to 10 membered heteroaromatic ring, which contains 1, 2, 3 or 4 heteroatoms selected from O, S and N.

More preferably an Indanyl- or Tetrahydronaphthyl-amino-azoline compound of formula I, wherein $R^1$ is hydrogen.

An Indanyl- or Tetrahydronaphthyl-amino-azoline compound of formula I, wherein $R^2$ is selected from cyano, azido, halogen, OH, SH, $NH_2$, $CONH_2$, $SO_3H$, COOH, C(=O)$R^{2c}$, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, ($C_1$-$C_6$-alkyl)amino, di($C_1$-$C_6$-alkyl)amino, wherein the carbon atoms in the aliphatic radicals of the aforementioned groups may carry any combination of 1, 2 or 3 radicals, independently of one another selected from the group consisting of halogen, cyano, nitro, hydroxy, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and wherein $R^{2c}$ is selected from hydrogen, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, ($C_1$-$C_6$-alkyl)amino, di($C_1$-$C_6$-alkyl)amino, phenyl and heteroaryl, which can be a mono- or bicyclic 5 to 10 membered heteroaromatic ring, which contains 1, 2, 3 or 4 heteroatoms selected from O, S and N.

More preferably an Indanyl- or Tetrahydronaphthyl-amino-azoline compound of formula I, wherein $R^2$ is selected from halogen, $C_1$-$C_6$-alkyl, $C_2$-$C_6$-alkenyl, $C_2$-$C_6$-alkinyl, $C_1$-$C_6$-alkoxy or $C_3$-$C_8$-cycloalkyl, wherein the radicals may be unsubstituted, partially or fully halogenated.

An Indanyl- or Tetrahydronaphthyl-amino-azoline compound of formula I, wherein m is 3 and $R^2$ is substituted at positions A, C and D.

An Indanyl- or Tetrahydronaphthyl-amino-azoline compound of formula I, wherein m is 2 and $R^2$ is substituted at positions A and C.

An Indanyl- or Tetrahydronaphthyl-amino-azoline compound of formula I, wherein m is 2 and $R^2$ is substituted at positions C and D.

An Indanyl- or Tetrahydronaphthyl-amino-azoline compound of formula I, wherein m is 1 and $R^2$ is substituted at position A.

An Indanyl- or Tetrahydronaphthyl-amino-azoline compound of formula I, wherein m is 1 and $R^2$ is substituted at position C.

An Indanyl- or Tetrahydronaphthyl-amino-azoline compound of formula I, wherein X is S or O.

An Indanyl- or Tetrahydronaphthyl-amino-azoline compound of formula I, wherein X is S.

Preferred are Indanyl-amino-azoline compounds of formula I, wherein n is 1.

The compound of the present invention can be e.g. prepared from the corresponding amines II by the synthetic route outlined in the following scheme:

1-Chloro-2-isothiocyanatoethane (CAS-reg.-no.: 6099-88-3) and 2-chloroethylisocyanate (CAS-reg.-no.: 1943-83-5) are commercially available.

Compounds of the general formula VI or VII can be obtained by reaction with a suitable electrophile as outlined in the following scheme e.g. an alkylating or acylating reagent e.g. as described in WO 2005063724.

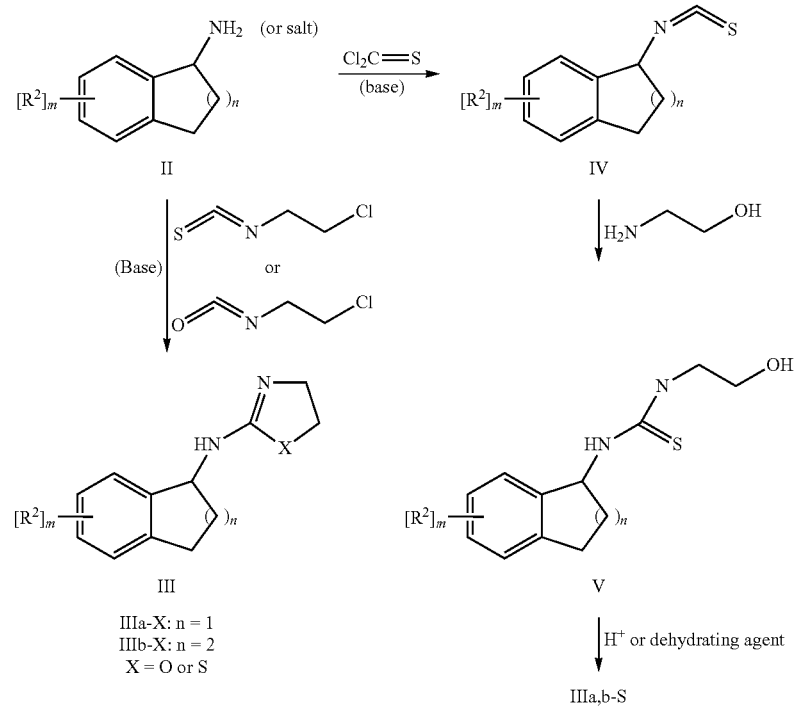

According to the method outlined in the scheme, an amine II is converted to the corresponding isothiocyanate IV by conventional means, e.g. by reacting II with thiophosgene (see e.g. Houben-Weyl, E4, "Methoden der Organischen Chemie", chapter IIc, pp. 837-842, Georg Thieme Verlag 1983. The isothiocyanate IV is then reacted with aminoethanol, thereby obtaining the thiourea V.

The reaction of the aminoethanol with isothiocyanate IV can be performed in accordance with standard methods of organic chemistry, see e.g. Biosci. Biotech. Biochem. 56 (7), 1062-65 (1992).

The thus obtained thioureas V can be cyclized by conventional means thereby obtaining the desired thiazoline compound of the formula IIIa,b-S. Cyclization of compound V can be achieved e.g. under acid catalysis or under dehydrating conditions e.g. by Mitsunobu's reaction (see Tetrahedron Letters 1999, 40, 3125-3128).

In our parallel US provisional application, which is filed simultaneously, such alternatives methods are described.

According to the method outlined in the scheme, an amine II can also be converted to azolines III-X by reaction with 2-chloroethylisothiocyanate or 2-chloroethylisocyanate e.g. as described in Bioorg. Med. Chem. Lett. 1994, 4, 2317-22 and subsequent cyclization in the presence or absence of base or under the conditions described below.

Amines II are commercially available or known in the art or can be prepared by methods familiar to an organic chemist and well known in the art e.g. EP 2812578 (indanyl type amines) or U.S. Pat. No. 3,953,506 (tetrahydronaphthyl type amines).

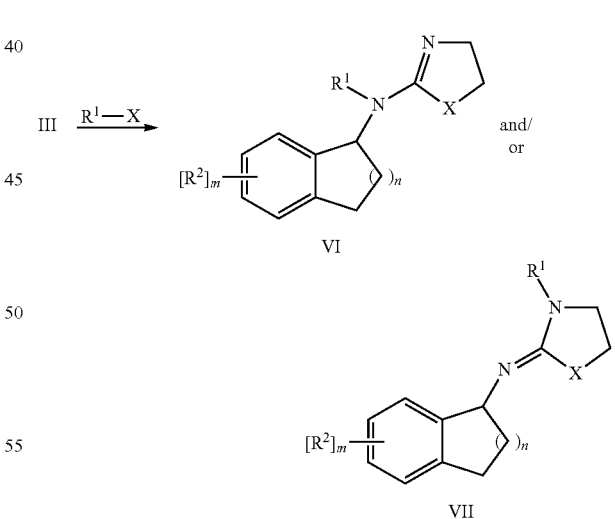

The particular reaction mixtures are worked up, as a rule, by conventional methods, for example by removing the solvent, distributing the residue in a mixture of water and a suitable organic solvent and isolating the product from the organic phase.

The Indanyl- or Tetrahydronaphthyl-amino-azoline compounds I may be obtained in the preparation as isomer mixtures, which however can, if desired, be separated into the pure isomers by conventional methods, for example by crystallization or chromatography (if necessary, over an optically active adsorbate). Pure optically active isomers can be synthesized, for example, from corresponding optically active starting materials.

In general, the Indanyl- or Tetrahydronaphthyl-amino-azoline compounds of the formula I can be prepared by the methods described above. However, in individual cases, certain compounds I can also advantageously be prepared from other compounds by other conventional methods as ester hydrolysis, amidation, esterification, ether cleavage, olefination, reduction, oxidation etc.

Preferred examples of compounds of formula I of the present invention are represented in the following:

1. Formula I-A

Amongst compounds of the formula I, preference is given to the following compounds of the formula I-A, wherein n=1, $R^1$=H with X being S:

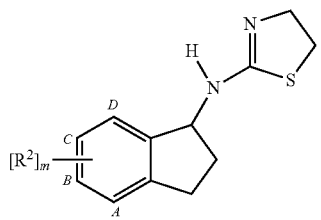

(I-A)

wherein the variables m and $R^2$ have the meanings given below. Examples of these compounds are those where $[R^2]_m$ has the meaning given in each line of table A (Compounds I-A.1 to I-A.72).

TABLE A

| Position of $R^2$: | $[R^2]_m$ | | | |
|---|---|---|---|---|
| | A | B | C | D |
| compound I-A.1 | CH₃ | — | — | — |
| compound I-A.2 | — | CH₃ | — | — |
| compound I-A.3 | — | — | CH₃ | — |
| compound I-A.4 | — | — | — | CH₃ |
| compound I-A.5 | CH₃ | — | CH₃ | — |
| compound I-A.6 | CH₃ | — | CH₃ | CH₃ |
| compound I-A.7 | — | — | CH₃ | CH₃ |
| compound I-A.8 | Cl | — | — | — |
| compound I-A.9 | — | Cl | — | — |
| compound I-A.10 | — | — | Cl | — |
| compound I-A.11 | — | — | — | Cl |
| compound I-A.12 | Cl | — | Cl | — |
| compound I-A.13 | Cl | — | Cl | Cl |
| compound I-A.14 | — | — | Cl | Cl |
| compound I-A.15 | F | — | — | — |
| compound I-A.16 | — | F | — | — |
| compound I-A.17 | — | — | F | — |
| compound I-A.18 | — | — | — | F |
| compound I-A.19 | F | — | F | — |
| compound I-A.20 | F | — | F | F |
| compound I-A.21 | — | — | F | F |
| compound I-A.22 | Br | — | — | — |
| compound I-A.23 | — | Br | — | — |
| compound I-A.24 | — | — | Br | — |
| compound I-A.25 | — | — | — | Br |
| compound I-A.26 | Br | — | Br | — |
| compound I-A.27 | Br | — | Br | Br |
| compound I-A.28 | — | — | Br | Br |
| compound I-A.29 | CF₃ | — | — | — |
| compound I-A.30 | — | CF₃ | — | — |
| compound I-A.31 | — | — | CF₃ | — |
| compound I-A.32 | — | — | — | CF₃ |

TABLE A-continued

| Position of $R^2$: | $[R^2]_m$ | | | |
|---|---|---|---|---|
| | A | B | C | D |
| compound I-A.33 | CF₃ | — | CF₃ | — |
| compound I-A.34 | CF₃ | — | CF₃ | CF₃ |
| compound I-A.35 | — | — | CF₃ | CF₃ |
| compound I-A.36 | OCF₃ | — | — | — |
| compound I-A.37 | — | OCF₃ | — | — |
| compound I-A.38 | — | — | OCF₃ | — |
| compound I-A.39 | — | — | — | OCF₃ |
| compound I-A.40 | OCF₃ | — | OCF₃ | — |
| compound I-A.41 | OCF₃ | — | OCF₃ | OCF₃ |
| compound I-A.42 | — | — | OCF₃ | OCF₃ |
| compound I-A.43 | CH₃ | — | Cl | — |
| compound I-A.44 | Cl | — | CH₃ | — |
| compound I-A.45 | CH₃ | — | F | — |
| compound I-A.46 | F | — | CH₃ | — |
| compound I-A.47 | CH₃ | — | Br | — |
| compound I-A.48 | Br | — | CH₃ | — |
| compound I-A.49 | CH₃ | — | CF₃ | — |
| compound I-A.50 | CF₃ | — | CH₃ | — |
| compound I-A.51 | CH₃ | — | OCF₃ | — |
| compound I-A.52 | OCF₃ | — | CH₃ | — |
| compound I-A.53 | Cl | — | F | — |
| compound I-A.54 | F | — | Cl | — |
| compound I-A.55 | Cl | — | Br | — |
| compound I-A.56 | Br | — | Cl | — |
| compound I-A.57 | Cl | — | CF₃ | — |
| compound I-A.58 | CF₃ | — | Cl | — |
| compound I-A.59 | Cl | — | OCF₃ | — |
| compound I-A.60 | OCF₃ | — | Cl | — |
| compound I-A.61 | F | — | Br | — |
| compound I-A.62 | Br | — | F | — |
| compound I-A.63 | F | — | CF₃ | — |
| compound I-A.64 | CF₃ | — | F | — |
| compound I-A.65 | F | — | OCF₃ | — |
| compound I-A.66 | OCF₃ | — | F | — |
| compound I-A.67 | Br | — | CF₃ | — |
| compound I-A.68 | CF₃ | — | Br | — |
| compound I-A.69 | Br | — | OCF₃ | — |
| compound I-A.70 | OCF₃ | — | Br | — |
| compound I-A.71 | CF₃ | — | OCF₃ | — |
| compound I-A.72 | OCF₃ | — | CF₃ | — |

2. Formula I-B

Amongst compounds of the formula I, preference is given to the following compounds of the formula I-B, wherein n=1, $R^1$=H and X=O, and wherein the variables m and $R^2$ have the meanings given below.

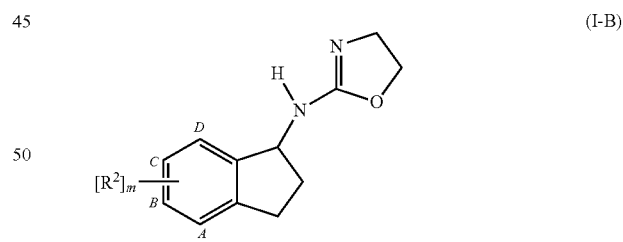

(I-B)

Examples of these compounds are those where $[R^2]_m$ has the meaning given in each line of table B (Compounds I-B.1 to I-B.72).

TABLE B

| Position of $R^2$: | $[R^2]_m$ | | | |
|---|---|---|---|---|
| | A | B | C | D |
| compound I-B.1 | CH₃ | — | — | — |
| compound I-B.2 | — | CH₃ | — | — |
| compound I-B.3 | — | — | CH₃ | — |
| compound I-B.4 | — | — | — | CH₃ |

TABLE B-continued

| Position of R²: | A | B | C | D |
| --- | --- | --- | --- | --- |
| compound I-B.5 | CH₃ | — | CH₃ | — |
| compound I-B.6 | CH₃ | — | CH₃ | CH₃ |
| compound I-B.7 | — | — | CH₃ | CH₃ |
| compound I-B.8 | Cl | — | — | — |
| compound I-B.9 | — | Cl | — | — |
| compound I-B.10 | — | — | Cl | — |
| compound I-B.11 | — | — | — | Cl |
| compound I-B.12 | Cl | — | Cl | — |
| compound I-B.13 | Cl | — | Cl | Cl |
| compound I-B.14 | — | — | Cl | Cl |
| compound I-B.15 | F | — | — | — |
| compound I-B.16 | — | F | — | — |
| compound I-B.17 | — | — | F | — |
| compound I-B.18 | — | — | — | F |
| compound I-B.19 | F | — | F | — |
| compound I-B.20 | F | — | F | F |
| compound I-B.21 | — | — | F | F |
| compound I-B.22 | Br | — | — | — |
| compound I-B.23 | — | Br | — | — |
| compound I-B.24 | — | — | Br | — |
| compound I-B.25 | — | — | — | Br |
| compound I-B.26 | Br | — | Br | — |
| compound I-B.27 | Br | — | Br | Br |
| compound I-B.28 | — | — | Br | Br |
| compound I-B.29 | CF₃ | — | — | — |
| compound I-B.30 | — | CF₃ | — | — |
| compound I-B.31 | — | — | CF₃ | — |
| compound I-B.32 | — | — | — | CF₃ |
| compound I-B.33 | CF₃ | — | CF₃ | — |
| compound I-B.34 | CF₃ | — | CF₃ | CF₃ |
| compound I-B.35 | — | — | CF₃ | CF₃ |
| compound I-B.36 | OCF₃ | — | — | — |
| compound I-B.37 | — | OCF₃ | — | — |
| compound I-B.38 | — | — | OCF₃ | — |
| compound I-B.39 | — | — | — | OCF₃ |
| compound I-B.40 | OCF₃ | — | OCF₃ | — |
| compound I-B.41 | OCF₃ | — | OCF₃ | OCF₃ |
| compound I-B.42 | — | — | OCF₃ | OCF₃ |
| compound I-B.43 | CH₃ | — | Cl | — |
| compound I-B.44 | Cl | — | CH₃ | — |
| compound I-B.45 | CH₃ | — | F | — |
| compound I-B.46 | F | — | CH₃ | — |
| compound I-B.47 | CH₃ | — | Br | — |
| compound I-B.48 | Br | — | CH₃ | — |
| compound I-B.49 | CH₃ | — | CF₃ | — |
| compound I-B.50 | CF₃ | — | CH₃ | — |
| compound I-B.51 | CH₃ | — | OCF₃ | — |
| compound I-B.52 | OCF₃ | — | CH₃ | — |
| compound I-B.53 | Cl | — | F | — |
| compound I-B.54 | F | — | Cl | — |
| compound I-B.55 | Cl | — | Br | — |
| compound I-B.56 | Br | — | Cl | — |
| compound I-B.57 | Cl | — | CF₃ | — |
| compound I-B.58 | CF₃ | — | Cl | — |
| compound I-B.59 | Cl | — | OCF₃ | — |
| compound I-B.60 | OCF₃ | — | Cl | — |
| compound I-B.61 | F | — | Br | — |
| compound I-B.62 | Br | — | F | — |
| compound I-B.63 | F | — | CF₃ | — |
| compound I-B.64 | CF₃ | — | F | — |
| compound I-B.65 | F | — | OCF₃ | — |
| compound I-B.66 | OCF₃ | — | F | — |
| compound I-B.67 | Br | — | CF₃ | — |
| compound I-B.68 | CF₃ | — | Br | — |
| compound I-B.69 | Br | — | OCF₃ | — |
| compound I-B.70 | OCF₃ | — | Br | — |
| compound I-B.71 | CF₃ | — | OCF₃ | — |
| compound I-B.72 | OCF₃ | — | CF₃ | — |

3. Formula I-C

Amongst compounds of the formula I, preference is given to the following compounds of the formula I-C, wherein n=1, $R^1$=H and X=N—CH₃, and wherein the variables m and $R^2$ have the meanings given below.

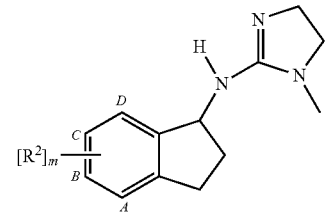

(I-C)

Examples of these compounds are those where $[R^2]_m$ has the meaning given in each line of table C (Compounds I-C.1 to I-C.72).

TABLE C

| Position of R²: | A | B | C | D |
| --- | --- | --- | --- | --- |
| compound I-C.1 | CH₃ | — | — | — |
| compound I-C.2 | — | CH₃ | — | — |
| compound I-C.3 | — | — | CH₃ | — |
| compound I-C.4 | — | — | — | CH₃ |
| compound I-C.5 | CH₃ | — | CH₃ | — |
| compound I-C.6 | CH₃ | — | CH₃ | CH₃ |
| compound I-C.7 | — | — | CH₃ | CH₃ |
| compound I-C.8 | Cl | — | — | — |
| compound I-C.9 | — | Cl | — | — |
| compound I-C.10 | — | — | Cl | — |
| compound I-C.11 | — | — | — | Cl |
| compound I-C.12 | Cl | — | Cl | — |
| compound I-C.13 | Cl | — | Cl | Cl |
| compound I-C.14 | — | — | Cl | Cl |
| compound I-C.15 | F | — | — | — |
| compound I-C.16 | — | F | — | — |
| compound I-C.17 | — | — | F | — |
| compound I-C.18 | — | — | — | F |
| compound I-C.19 | F | — | F | — |
| compound I-C.20 | F | — | F | F |
| compound I-C.21 | — | — | F | F |
| compound I-C.22 | Br | — | — | — |
| compound I-C.23 | — | Br | — | — |
| compound I-C.24 | — | — | Br | — |
| compound I-C.25 | — | — | — | Br |
| compound I-C.26 | Br | — | Br | — |
| compound I-C.27 | Br | — | Br | Br |
| compound I-C.28 | — | — | Br | Br |
| compound I-C.29 | CF₃ | — | — | — |
| compound I-C.30 | — | CF₃ | — | — |
| compound I-C.31 | — | — | CF₃ | — |
| compound I-C.32 | — | — | — | CF₃ |
| compound I-C.33 | CF₃ | — | CF₃ | — |
| compound I-C.34 | CF₃ | — | CF₃ | CF₃ |
| compound I-C.35 | — | — | CF₃ | CF₃ |
| compound I-C.36 | OCF₃ | — | — | — |
| compound I-C.37 | — | OCF₃ | — | — |
| compound I-C.38 | — | — | OCF₃ | — |
| compound I-C.39 | — | — | — | OCF₃ |
| compound I-C.40 | OCF₃ | — | OCF₃ | — |
| compound I-C.41 | OCF₃ | — | OCF₃ | OCF₃ |
| compound I-C.42 | — | — | OCF₃ | OCF₃ |
| compound I-C.43 | CH₃ | — | Cl | — |
| compound I-C.44 | Cl | — | CH₃ | — |
| compound I-C.45 | CH₃ | — | F | — |
| compound I-C.46 | F | — | CH₃ | — |
| compound I-C.47 | CH₃ | — | Br | — |
| compound I-C.48 | Br | — | CH₃ | — |
| compound I-C.49 | CH₃ | — | CF₃ | — |
| compound I-C.50 | CF₃ | — | CH₃ | — |
| compound I-C.51 | CH₃ | — | OCF₃ | — |
| compound I-C.52 | OCF₃ | — | CH₃ | — |
| compound I-C.53 | Cl | — | F | — |

TABLE C-continued

| Position of R²: | A | B | C | D |
|---|---|---|---|---|
| compound I-C.54 | F | — | Cl | — |
| compound I-C.55 | Cl | — | Br | — |
| compound I-C.56 | Br | — | Cl | — |
| compound I-C.57 | Cl | — | CF₃ | — |
| compound I-C.58 | CF₃ | — | Cl | — |
| compound I-C.59 | Cl | — | OCF₃ | — |
| compound I-C.60 | OCF₃ | — | Cl | — |
| compound I-C.61 | F | — | Br | — |
| compound I-C.62 | Br | — | F | — |
| compound I-C.63 | F | — | CF₃ | — |
| compound I-C.64 | CF₃ | — | F | — |
| compound I-C.65 | F | — | OCF₃ | — |
| compound I-C.66 | OCF₃ | — | F | — |
| compound I-C.67 | Br | — | CF₃ | — |
| compound I-C.68 | CF₃ | — | Br | — |
| compound I-C.69 | Br | — | OCF₃ | — |
| compound I-C.70 | OCF₃ | — | Br | — |
| compound I-C.71 | CF₃ | — | OCF₃ | — |
| compound I-C.72 | OCF₃ | — | CF₃ | — |

4. Formula I-D

Amongst compounds of the formula I, preference is given to the following compounds of the formula I-D, wherein n=2, $R^1$=H and X=S:

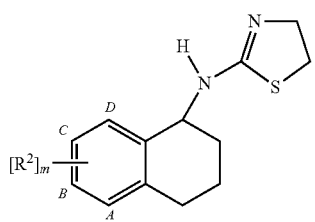

(I-D)

wherein the variables m and $R^2$ have the meanings given below.

Examples of these compounds are those where $[R^2]_m$ has the meaning given in each line of table D (Compounds I-D.1 to I-D.72).

TABLE D

| Position of R²: | A | B | C | D |
|---|---|---|---|---|
| compound I-D.1 | CH₃ | — | — | — |
| compound I-D.2 | — | CH₃ | — | — |
| compound I-D.3 | — | — | CH₃ | — |
| compound I-D.4 | — | — | — | CH₃ |
| compound I-D.5 | CH₃ | — | CH₃ | — |
| compound I-D.6 | CH₃ | — | CH₃ | CH₃ |
| compound I-D.7 | — | — | CH₃ | CH₃ |
| compound I-D.8 | Cl | — | — | — |
| compound I-D.9 | — | Cl | — | — |
| compound I-D.10 | — | — | Cl | — |
| compound I-D.11 | — | — | — | Cl |
| compound I-D.12 | Cl | — | Cl | — |
| compound I-D.13 | Cl | — | Cl | Cl |
| compound I-D.14 | — | — | Cl | Cl |
| compound I-D.15 | F | — | — | — |
| compound I-D.16 | — | F | — | — |
| compound I-D.17 | — | — | F | — |
| compound I-D.18 | — | — | — | F |
| compound I-D.19 | F | — | F | — |
| compound I-D.20 | F | — | F | F |
| compound I-D.21 | — | — | F | F |
| compound I-D.22 | Br | — | — | — |
| compound I-D.23 | — | Br | — | — |
| compound I-D.24 | — | — | Br | — |
| compound I-D.25 | — | — | — | Br |
| compound I-D.26 | Br | — | Br | — |
| compound I-D.27 | Br | — | Br | Br |
| compound I-D.28 | — | — | Br | Br |
| compound I-D.29 | CF₃ | — | — | — |
| compound I-D.30 | — | CF₃ | — | — |
| compound I-D.31 | — | — | CF₃ | — |
| compound I-D.32 | — | — | — | CF₃ |
| compound I-D.33 | CF₃ | — | CF₃ | — |
| compound I-D.34 | CF₃ | — | CF₃ | CF₃ |
| compound I-D.35 | — | — | CF₃ | CF₃ |
| compound I-D.36 | OCF₃ | — | — | — |
| compound I-D.37 | — | OCF₃ | — | — |
| compound I-D.38 | — | — | OCF₃ | — |
| compound I-D.39 | — | — | — | OCF₃ |
| compound I-D.40 | OCF₃ | — | OCF₃ | — |
| compound I-D.41 | OCF₃ | — | OCF₃ | OCF₃ |
| compound I-D.42 | — | — | OCF₃ | OCF₃ |
| compound I-D.43 | CH₃ | — | Cl | — |
| compound I-D.44 | Cl | — | CH₃ | — |
| compound I-D.45 | CH₃ | — | F | — |
| compound I-D.46 | F | — | CH₃ | — |
| compound I-D.47 | CH₃ | — | Br | — |
| compound I-D.48 | Br | — | CH₃ | — |
| compound I-D.49 | CH₃ | — | CF₃ | — |
| compound I-D.50 | CF₃ | — | CH₃ | — |
| compound I-D.51 | CH₃ | — | OCF₃ | — |
| compound I-D.52 | OCF₃ | — | CH₃ | — |
| compound I-D.53 | Cl | — | F | — |
| compound I-D.54 | F | — | Cl | — |
| compound I-D.55 | Cl | — | Br | — |
| compound I-D.56 | Br | — | Cl | — |
| compound I-D.57 | Cl | — | CF₃ | — |
| compound I-D.58 | CF₃ | — | Cl | — |
| compound I-D.59 | Cl | — | OCF₃ | — |
| compound I-D.60 | OCF₃ | — | Cl | — |
| compound I-D.61 | F | — | Br | — |
| compound I-D.62 | Br | — | F | — |
| compound I-D.63 | F | — | CF₃ | — |
| compound I-D.64 | CF₃ | — | F | — |
| compound I-D.65 | F | — | OCF₃ | — |
| compound I-D.66 | OCF₃ | — | F | — |
| compound I-D.67 | Br | — | CF₃ | — |
| compound I-D.68 | CF₃ | — | Br | — |
| compound I-D.69 | Br | — | OCF₃ | — |
| compound I-D.70 | OCF₃ | — | Br | — |
| compound I-D.71 | CF₃ | — | OCF₃ | — |
| compound I-D.72 | OCF₃ | — | CF₃ | — |

5. Formula I-E

Amongst compounds of the formula I, preference is given to the following compounds of the formula I-E, wherein n=2, $R^1$=H and X=O:

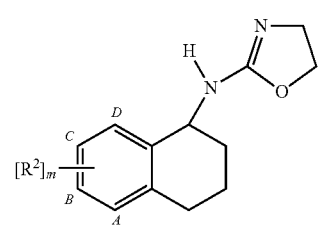

(I-E)

wherein the variables m and $R^2$ have the meanings given below. Examples of these compounds are those where $[R^2]_m$ has the meaning given in each line of table E (Compounds I-E.1 to I-E.72).

TABLE E

| Position of $R^2$: | A | B | C | D |
|---|---|---|---|---|
| compound I-E.1 | $CH_3$ | — | — | — |
| compound I-E.2 | — | $CH_3$ | — | — |
| compound I-E.3 | — | — | $CH_3$ | — |
| compound I-E.4 | — | — | — | $CH_3$ |
| compound I-E.5 | $CH_3$ | — | $CH_3$ | — |
| compound I-E.6 | $CH_3$ | — | $CH_3$ | $CH_3$ |
| compound I-E.7 | — | — | $CH_3$ | $CH_3$ |
| compound I-E.8 | Cl | — | — | — |
| compound I-E.9 | — | Cl | — | — |
| compound I-E.10 | — | — | Cl | — |
| compound I-E.11 | — | — | — | Cl |
| compound I-E.12 | Cl | — | Cl | — |
| compound I-E.13 | Cl | — | Cl | Cl |
| compound I-E.14 | — | — | Cl | Cl |
| compound I-E.15 | F | — | — | — |
| compound I-E.16 | — | F | — | — |
| compound I-E.17 | — | — | F | — |
| compound I-E.18 | — | — | — | F |
| compound I-E.19 | F | — | F | — |
| compound I-E.20 | F | — | F | F |
| compound I-E.21 | — | — | F | F |
| compound I-E.22 | Br | — | — | — |
| compound I-E.23 | — | Br | — | — |
| compound I-E.24 | — | — | Br | — |
| compound I-E.25 | — | — | — | Br |
| compound I-E.26 | Br | — | Br | — |
| compound I-E.27 | Br | — | Br | Br |
| compound I-E.28 | — | — | Br | Br |
| compound I-E.29 | $CF_3$ | — | — | — |
| compound I-E.30 | — | $CF_3$ | — | — |
| compound I-E.31 | — | — | $CF_3$ | — |
| compound I-E.32 | — | — | — | $CF_3$ |
| compound I-E.33 | $CF_3$ | — | $CF_3$ | — |
| compound I-E.34 | $CF_3$ | — | $CF_3$ | $CF_3$ |
| compound I-E.35 | — | — | $CF_3$ | $CF_3$ |
| compound I-E.36 | $OCF_3$ | — | — | — |
| compound I-E.37 | — | $OCF_3$ | — | — |
| compound I-E.38 | — | — | $OCF_3$ | — |
| compound I-E.39 | — | — | — | $OCF_3$ |
| compound I-E.40 | $OCF_3$ | — | $OCF_3$ | — |
| compound I-E.41 | $OCF_3$ | — | $OCF_3$ | $OCF_3$ |
| compound I-E.42 | — | — | $OCF_3$ | $OCF_3$ |
| compound I-E.43 | $CH_3$ | — | Cl | — |
| compound I-E.44 | Cl | — | $CH_3$ | — |
| compound I-E.45 | $CH_3$ | — | F | — |
| compound I-E.46 | F | — | $CH_3$ | — |
| compound I-E.47 | $CH_3$ | — | Br | — |
| compound I-E.48 | Br | — | $CH_3$ | — |
| compound I-E.49 | $CH_3$ | — | $CF_3$ | — |
| compound I-E.50 | $CF_3$ | — | $CH_3$ | — |
| compound I-E.51 | $CH_3$ | — | $OCF_3$ | — |
| compound I-E.52 | $OCF_3$ | — | $CH_3$ | — |
| compound I-E.53 | Cl | — | F | — |
| compound I-E.54 | F | — | Cl | — |
| compound I-E.55 | Cl | — | Br | — |
| compound I-E.56 | Br | — | Cl | — |
| compound I-E.57 | Cl | — | $CF_3$ | — |
| compound I-E.58 | $CF_3$ | — | Cl | — |
| compound I-E.59 | Cl | — | $OCF_3$ | — |
| compound I-E.60 | $OCF_3$ | — | Cl | — |
| compound I-E.61 | F | — | Br | — |
| compound I-E.62 | Br | — | F | — |
| compound I-E.63 | F | — | $CF_3$ | — |
| compound I-E.64 | $CF_3$ | — | F | — |
| compound I-E.65 | F | — | $OCF_3$ | — |
| compound I-E.66 | $OCF_3$ | — | F | — |
| compound I-E.67 | Br | — | $CF_3$ | — |
| compound I-E.68 | $CF_3$ | — | Br | — |
| compound I-E.69 | Br | — | $OCF_3$ | — |
| compound I-E.70 | $OCF_3$ | — | Br | — |

TABLE E-continued

| Position of $R^2$: | A | B | C | D |
|---|---|---|---|---|
| compound I-E.71 | $CF_3$ | — | $OCF_3$ | — |
| compound I-E.72 | $OCF_3$ | — | $CF_3$ | — |

6. Formula I-F

Amongst compounds of the formula I, preference is given to the following compounds of the formula I-F, wherein n=2, $R^1$=H and X=N—$CH_3$:

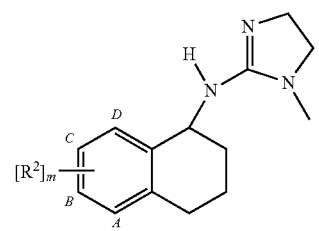

(I-F)

wherein the variables m and $R^2$ have the meanings given below. Examples of these compounds are those where $[R^2]_m$ has the meaning given in each line of table F (Compounds I-F.1 to I-F.72).

TABLE F

| Position of $R^2$: | A | B | C | D |
|---|---|---|---|---|
| compound I-F.1 | $CH_3$ | — | — | — |
| compound I-F.2 | — | $CH_3$ | — | — |
| compound I-F.3 | — | — | $CH_3$ | — |
| compound I-F.4 | — | — | — | $CH_3$ |
| compound I-F.5 | $CH_3$ | — | $CH_3$ | — |
| compound I-F.6 | $CH_3$ | — | $CH_3$ | $CH_3$ |
| compound I-F.7 | — | — | $CH_3$ | $CH_3$ |
| compound I-F.8 | Cl | — | — | — |
| compound I-F.9 | — | Cl | — | — |
| compound I-F.10 | — | — | Cl | — |
| compound I-F.11 | — | — | — | Cl |
| compound I-F.12 | Cl | — | Cl | — |
| compound I-F.13 | Cl | — | Cl | Cl |
| compound I-F.14 | — | — | Cl | Cl |
| compound I-F.15 | F | — | — | — |
| compound I-F.16 | — | F | — | — |
| compound I-F.17 | — | — | F | — |
| compound I-F.18 | — | — | — | F |
| compound I-F.19 | F | — | F | — |
| compound I-F.20 | F | — | F | F |
| compound I-F.21 | — | — | F | F |
| compound I-F.22 | Br | — | — | — |
| compound I-F.23 | — | Br | — | — |
| compound I-F.24 | — | — | Br | — |
| compound I-F.25 | — | — | — | Br |
| compound I-F.26 | Br | — | Br | — |
| compound I-F.27 | Br | — | Br | Br |
| compound I-F.28 | — | — | Br | Br |
| compound I-F.29 | $CF_3$ | — | — | — |
| compound I-F.30 | — | $CF_3$ | — | — |
| compound I-F.31 | — | — | $CF_3$ | — |
| compound I-F.32 | — | — | — | $CF_3$ |
| compound I-F.33 | $CF_3$ | — | $CF_3$ | — |
| compound I-F.34 | $CF_3$ | — | $CF_3$ | $CF_3$ |
| compound I-F.35 | — | — | $CF_3$ | $CF_3$ |
| compound I-F.36 | $OCF_3$ | — | — | — |
| compound I-F.37 | — | $OCF_3$ | — | — |
| compound I-F.38 | — | — | $OCF_3$ | — |
| compound I-F.39 | — | — | — | $OCF_3$ |

TABLE F-continued

| Position of $R^2$: | A | B | C | D |
|---|---|---|---|---|
| compound I-F.40 | OCF$_3$ | — | OCF$_3$ | — |
| compound I-F.41 | OCF$_3$ | — | OCF$_3$ | OCF$_3$ |
| compound I-F.42 | — | — | OCF$_3$ | OCF$_3$ |
| compound I-F.43 | CH$_3$ | — | Cl | — |
| compound I-F.44 | Cl | — | CH$_3$ | — |
| compound I-F.45 | CH$_3$ | — | F | — |
| compound I-F.46 | F | — | CH$_3$ | — |
| compound I-F.47 | CH$_3$ | — | Br | — |
| compound I-F.48 | Br | — | CH$_3$ | — |
| compound I-F.49 | CH$_3$ | — | CF$_3$ | — |
| compound I-F.50 | CF$_3$ | — | CH$_3$ | — |
| compound I-F.51 | CH$_3$ | — | OCF$_3$ | — |
| compound I-F.52 | OCF$_3$ | — | CH$_3$ | — |
| compound I-F.53 | Cl | — | F | — |
| compound I-F.54 | F | — | Cl | — |
| compound I-F.55 | Cl | — | Br | — |
| compound I-F.56 | Br | — | Cl | — |
| compound I-F.57 | Cl | — | CF$_3$ | — |
| compound I-F.58 | CF$_3$ | — | Cl | — |
| compound I-F.59 | Cl | — | OCF$_3$ | — |
| compound I-F.60 | OCF$_3$ | — | Cl | — |
| compound I-F.61 | F | — | Br | — |
| compound I-F.62 | Br | — | F | — |
| compound I-F.63 | F | — | CF$_3$ | — |
| compound I-F.64 | CF$_3$ | — | F | — |
| compound I-F.65 | F | — | OCF$_3$ | — |
| compound I-F.66 | OCF$_3$ | — | F | — |
| compound I-F.67 | Br | — | CF$_3$ | — |
| compound I-F.68 | CF$_3$ | — | Br | — |
| compound I-F.69 | Br | — | OCF$_3$ | — |
| compound I-F.70 | OCF$_3$ | — | Br | — |
| compound I-F.71 | CF$_3$ | — | OCF$_3$ | — |
| compound I-F.72 | OCF$_3$ | — | CF$_3$ | — |

7. Formula I-G

Amongst compounds of the formula I, preference is given to the following compounds of the formula I-G, wherein n=1, $R^1$=H$_3$C—CO and X=S,

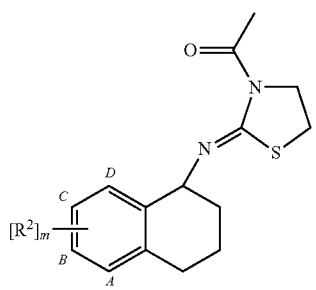

(I-G)

wherein the variables m and $R^2$ have the meanings given below. Examples of these compounds are those where $[R^2]_m$ has the meaning given in each line of table G (Compounds I-G.1 to I-G.72).

TABLE G

| Position of $R^2$: | A | B | C | D |
|---|---|---|---|---|
| compound I-G.1 | CH$_3$ | — | — | — |
| compound I-G.2 | — | CH$_3$ | — | — |
| compound I-G.3 | — | — | CH$_3$ | — |
| compound I-G.4 | — | — | — | CH$_3$ |
| compound I-G.5 | CH$_3$ | — | CH$_3$ | — |
| compound I-G.6 | CH$_3$ | — | CH$_3$ | CH$_3$ |
| compound I-G.7 | — | — | CH$_3$ | CH$_3$ |
| compound I-G.8 | Cl | — | — | — |
| compound I-G.9 | — | Cl | — | — |
| compound I-G.10 | — | — | Cl | — |
| compound I-G.11 | — | — | — | Cl |
| compound I-G.12 | Cl | — | Cl | — |
| compound I-G.13 | Cl | — | Cl | Cl |
| compound I-G.14 | — | — | Cl | Cl |
| compound I-G.15 | F | — | — | — |
| compound I-G.16 | — | F | — | — |
| compound I-G.17 | — | — | F | — |
| compound I-G.18 | — | — | — | F |
| compound I-G.19 | F | — | F | — |
| compound I-G.20 | F | — | F | F |
| compound I-G.21 | — | — | F | F |
| compound I-G.22 | Br | — | — | — |
| compound I-G.23 | — | Br | — | — |
| compound I-G.24 | — | — | Br | — |
| compound I-G.25 | — | — | — | Br |
| compound I-G.26 | Br | — | Br | — |
| compound I-G.27 | Br | — | Br | Br |
| compound I-G.28 | — | — | Br | Br |
| compound I-G.29 | CF$_3$ | — | — | — |
| compound I-G.30 | — | CF$_3$ | — | — |
| compound I-G.31 | — | — | CF$_3$ | — |
| compound I-G.32 | — | — | — | CF$_3$ |
| compound I-G.33 | CF$_3$ | — | CF$_3$ | — |
| compound I-G.34 | CF$_3$ | — | CF$_3$ | CF$_3$ |
| compound I-G.35 | — | — | CF$_3$ | CF$_3$ |
| compound I-G.36 | OCF$_3$ | — | — | — |
| compound I-G.37 | — | OCF$_3$ | — | — |
| compound I-G.38 | — | — | OCF$_3$ | — |
| compound I-G.39 | — | — | — | OCF$_3$ |
| compound I-G.40 | OCF$_3$ | — | OCF$_3$ | — |
| compound I-G.41 | OCF$_3$ | — | OCF$_3$ | OCF$_3$ |
| compound I-G.42 | — | — | OCF$_3$ | OCF$_3$ |
| compound I-G.43 | CH$_3$ | — | Cl | — |
| compound I-G.44 | Cl | — | CH$_3$ | — |
| compound I-G.45 | CH$_3$ | — | F | — |
| compound I-G.46 | F | — | CH$_3$ | — |
| compound I-G.47 | CH$_3$ | — | Br | — |
| compound I-G.48 | Br | — | CH$_3$ | — |
| compound I-G.49 | CH$_3$ | — | CF$_3$ | — |
| compound I-G.50 | CF$_3$ | — | CH$_3$ | — |
| compound I-G.51 | CH$_3$ | — | OCF$_3$ | — |
| compound I-G.52 | OCF$_3$ | — | CH$_3$ | — |
| compound I-G.53 | Cl | — | F | — |
| compound I-G.54 | F | — | Cl | — |
| compound I-G.55 | Cl | — | Br | — |
| compound I-G.56 | Br | — | Cl | — |
| compound I-G.57 | Cl | — | CF$_3$ | — |
| compound I-G.58 | CF$_3$ | — | Cl | — |
| compound I-G.59 | Cl | — | OCF$_3$ | — |
| compound I-G.60 | OCF$_3$ | — | Cl | — |
| compound I-G.61 | F | — | Br | — |
| compound I-G.62 | Br | — | F | — |
| compound I-G.63 | F | — | CF$_3$ | — |
| compound I-G.64 | CF$_3$ | — | F | — |
| compound I-G.65 | F | — | OCF$_3$ | — |
| compound I-G.66 | OCF$_3$ | — | F | — |
| compound I-G.67 | Br | — | CF$_3$ | — |
| compound I-G.68 | CF$_3$ | — | Br | — |
| compound I-G.69 | Br | — | OCF$_3$ | — |
| compound I-G.70 | OCF$_3$ | — | Br | — |
| compound I-G.71 | CF$_3$ | — | OCF$_3$ | — |
| compound I-G.72 | OCF$_3$ | — | CF$_3$ | — |

8. Formula I-H

Amongst compounds of the formula I, preference is given to the following compounds of the formula I-H, wherein n=1, $R^1=H_3C$ and X=S

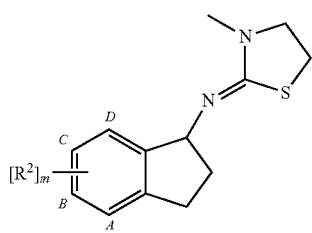

(I-H)

wherein the variables m and $R^2$ have the meanings given below. Examples of these compounds are those where $[R^2]_m$ has the meaning given in each line of table H (Compounds I-H.1 to 1-H.72).

TABLE H

| Position of $R^2$: | A | B | C | D |
|---|---|---|---|---|
| | | | $[R^2]_m$ | |
| compound I-H.1 | CH₃ | — | — | — |
| compound I-H.2 | — | CH₃ | — | — |
| compound I-H.3 | — | — | CH₃ | — |
| compound I-H.4 | — | — | — | CH₃ |
| compound I-H.5 | CH₃ | — | CH₃ | — |
| compound I-H.6 | CH₃ | — | CH₃ | CH₃ |
| compound I-H.7 | — | — | CH₃ | CH₃ |
| compound I-H.8 | Cl | — | — | — |
| compound I-H.9 | — | Cl | — | — |
| compound I-H.10 | — | — | Cl | — |
| compound I-H.11 | — | — | — | Cl |
| compound I-H.12 | Cl | — | Cl | — |
| compound I-H.13 | Cl | — | Cl | Cl |
| compound I-H.14 | — | — | Cl | Cl |
| compound I-H.15 | F | — | — | — |
| compound I-H.16 | — | F | — | — |
| compound I-H.17 | — | — | F | — |
| compound I-H.18 | — | — | — | F |
| compound I-H.19 | F | — | F | — |
| compound I-H.20 | F | — | F | F |
| compound I-H.21 | — | — | F | F |
| compound I-H.22 | Br | — | — | — |
| compound I-H.23 | — | Br | — | — |
| compound I-H.24 | — | — | Br | — |
| compound I-H.25 | — | — | — | Br |
| compound I-H.26 | Br | — | Br | — |
| compound I-H.27 | Br | — | Br | Br |
| compound I-H.28 | — | — | Br | Br |
| compound I-H.29 | CF₃ | — | — | — |
| compound I-H.30 | — | CF₃ | — | — |
| compound I-H.31 | — | — | CF₃ | — |
| compound I-H.32 | — | — | — | CF₃ |
| compound I-H.33 | CF₃ | — | CF₃ | — |
| compound I-H.34 | CF₃ | — | CF₃ | CF₃ |
| compound I-H.35 | — | — | CF₃ | CF₃ |
| compound I-H.36 | OCF₃ | — | — | — |
| compound I-H.37 | — | OCF₃ | — | — |
| compound I-H.38 | — | — | OCF₃ | — |
| compound I-H.39 | — | — | — | OCF₃ |
| compound I-H.40 | OCF₃ | — | OCF₃ | — |
| compound I-H.41 | OCF₃ | — | OCF₃ | OCF₃ |
| compound I-H.42 | — | — | OCF₃ | OCF₃ |
| compound I-H.43 | CH₃ | — | Cl | — |
| compound I-H.44 | Cl | — | CH₃ | — |
| compound I-H.45 | CH₃ | — | F | — |
| compound I-H.46 | F | — | CH₃ | — |
| compound I-H.47 | CH₃ | — | Br | — |
| compound I-H.48 | Br | — | CH₃ | — |
| compound I-H.49 | CH₃ | — | CF₃ | — |

TABLE H-continued

| Position of $R^2$: | A | B | C | D |
|---|---|---|---|---|
| | | | $[R^2]_m$ | |
| compound I-H.50 | CF₃ | — | CH₃ | — |
| compound I-H.51 | CH₃ | — | OCF₃ | — |
| compound I-H.52 | OCF₃ | — | CH₃ | — |
| compound I-H.53 | Cl | — | F | — |
| compound I-H.54 | F | — | Cl | — |
| compound I-H.55 | Cl | — | Br | — |
| compound I-H.56 | Br | — | Cl | — |
| compound I-H.57 | Cl | — | CF₃ | — |
| compound I-H.58 | CF₃ | — | Cl | — |
| compound I-H.59 | Cl | — | OCF₃ | — |
| compound I-H.60 | OCF₃ | — | Cl | — |
| compound I-H.61 | F | — | Br | — |
| compound I-H.62 | Br | — | F | — |
| compound I-H.63 | F | — | CF₃ | — |
| compound I-H.64 | CF₃ | — | F | — |
| compound I-H.65 | F | — | OCF₃ | — |
| compound I-H.66 | OCF₃ | — | F | — |
| compound I-H.67 | Br | — | CF₃ | — |
| compound I-H.68 | CF₃ | — | Br | — |
| compound I-H.69 | Br | — | OCF₃ | — |
| compound I-H.70 | OCF₃ | — | Br | — |
| compound I-H.71 | CF₃ | — | OCF₃ | — |
| compound I-H.72 | OCF₃ | — | CF₃ | — |

9. Formula I-I

Amongst compounds of the formula I, preference is given to the following compounds of the formula I-I, wherein n=1, $R^1$=CN and X=S

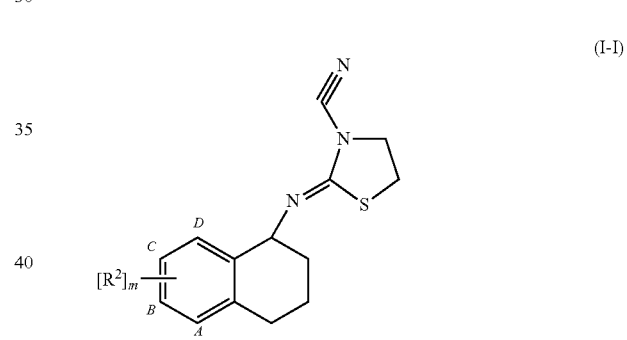

(I-I)

wherein the variables m and $R^2$ have the meanings given below. Examples of these compounds are those where $[R^2]_m$ has the meaning given in each line of table I (Compounds I-I.1 to I-I.72).

TABLE I

| Position of $R^2$: | A | B | C | D |
|---|---|---|---|---|
| | | | $[R^2]_m$ | |
| compound I-I.1 | CH₃ | — | — | — |
| compound I-I.2 | — | CH₃ | — | — |
| compound I-I.3 | — | — | CH₃ | — |
| compound I-I.4 | — | — | — | CH₃ |
| compound I-I.5 | CH₃ | — | CH₃ | — |
| compound I-I.6 | CH₃ | — | CH₃ | CH₃ |
| compound I-I.7 | — | — | CH₃ | CH₃ |
| compound I-I.8 | Cl | — | — | — |
| compound I-I.9 | — | Cl | — | — |
| compound I-I.10 | — | — | Cl | — |
| compound I-I.11 | — | — | — | Cl |
| compound I-I.12 | Cl | — | Cl | — |
| compound I-I.13 | Cl | — | Cl | Cl |
| compound I-I.14 | — | — | Cl | Cl |
| compound I-I.15 | F | — | — | — |

TABLE I-continued

| Position of $R^2$: | A | B | C | D |
|---|---|---|---|---|
| compound I-I.16 | — | F | — | — |
| compound I-I.17 | — | — | F | — |
| compound I-I.18 | — | — | — | F |
| compound I-I.19 | F | — | F | — |
| compound I-I.20 | F | — | F | F |
| compound I-I.21 | — | — | F | F |
| compound I-I.22 | Br | — | — | — |
| compound I-I.23 | — | Br | — | — |
| compound I-I.24 | — | — | Br | — |
| compound I-I.25 | — | — | — | Br |
| compound I-I.26 | Br | — | Br | — |
| compound I-I.27 | Br | — | Br | Br |
| compound I-I.28 | — | — | Br | Br |
| compound I-I.29 | $CF_3$ | — | — | — |
| compound I-I.30 | — | $CF_3$ | — | — |
| compound I-I.31 | — | — | $CF_3$ | — |
| compound I-I.32 | — | — | — | $CF_3$ |
| compound I-I.33 | $CF_3$ | — | $CF_3$ | — |
| compound I-I.34 | $CF_3$ | — | $CF_3$ | $CF_3$ |
| compound I-I.35 | — | — | $CF_3$ | $CF_3$ |
| compound I-I.36 | $OCF_3$ | — | — | — |
| compound I-I.37 | — | $OCF_3$ | — | — |
| compound I-I.38 | — | — | $OCF_3$ | — |
| compound I-I.39 | — | — | — | $OCF_3$ |
| compound I-I.40 | $OCF_3$ | — | $OCF_3$ | — |
| compound I-I.41 | $OCF_3$ | — | $OCF_3$ | $OCF_3$ |
| compound I-I.42 | — | — | $OCF_3$ | $OCF_3$ |
| compound I-I.43 | $CH_3$ | — | Cl | — |
| compound I-I.44 | Cl | — | $CH_3$ | — |
| compound I-I.45 | $CH_3$ | — | F | — |
| compound I-I.46 | F | — | $CH_3$ | — |
| compound I-I.47 | $CH_3$ | — | Br | — |
| compound I-I.48 | Br | — | $CH_3$ | — |
| compound I-I.49 | $CH_3$ | — | $CF_3$ | — |
| compound I-I.50 | $CF_3$ | — | $CH_3$ | — |
| compound I-I.51 | $CH_3$ | — | $OCF_3$ | — |
| compound I-I.52 | $OCF_3$ | — | $CH_3$ | — |
| compound I-I.53 | Cl | — | F | — |
| compound I-I.54 | F | — | Cl | — |
| compound I-I.55 | Cl | — | Br | — |
| compound I-I.56 | Br | — | Cl | — |
| compound I-I.57 | Cl | — | $CF_3$ | — |
| compound I-I.58 | $CF_3$ | — | Cl | — |
| compound I-I.59 | Cl | — | $OCF_3$ | — |
| compound I-I.60 | $OCF_3$ | — | Cl | — |
| compound I-I.61 | F | — | Br | — |
| compound I-I.62 | Br | — | F | — |
| compound I-I.63 | F | — | $CF_3$ | — |
| compound I-I.64 | $CF_3$ | — | F | — |
| compound I-I.65 | F | — | $OCF_3$ | — |
| compound I-I.66 | $OCF_3$ | — | F | — |
| compound I-I.67 | Br | — | $CF_3$ | — |
| compound I-I.68 | $CF_3$ | — | Br | — |
| compound I-I.69 | Br | — | $OCF_3$ | — |
| compound I-I.70 | $OCF_3$ | — | Br | — |
| compound I-I.71 | $CF_3$ | — | $OCF_3$ | — |
| compound I-I.72 | $OCF_3$ | — | $CF_3$ | — |

10. Formula I-J

Amongst compounds of the formula I, preference is given to the following compounds of the formula I-J, wherein n=2, $R^1=H_3C-CO$ and X=S:

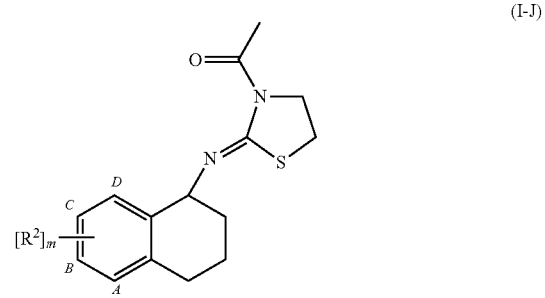

(I-J)

wherein the variables m and $R^2$ have the meanings given below. Examples of these compounds are those where $[R^2]_m$ has the meaning given in each line of table J (Compounds I-J.1 to I-J.72).

TABLE J

| Position of $R_2$: | A | B | C | D |
|---|---|---|---|---|
| compound I-J.1 | $CH_3$ | — | — | — |
| compound I-J.2 | — | $CH_3$ | — | — |
| compound I-J.3 | — | — | $CH_3$ | — |
| compound I-J.4 | — | — | — | $CH_3$ |
| compound I-J.5 | $CH_3$ | — | $CH_3$ | — |
| compound I-J.6 | $CH_3$ | — | $CH_3$ | $CH_3$ |
| compound I-J.7 | — | — | $CH_3$ | $CH_3$ |
| compound I-J.8 | Cl | — | — | — |
| compound I-J.9 | — | Cl | — | — |
| compound I-J.10 | — | — | Cl | — |
| compound I-J.11 | — | — | — | Cl |
| compound I-J.12 | Cl | — | Cl | — |
| compound I-J.13 | Cl | — | Cl | Cl |
| compound I-J.14 | — | — | Cl | Cl |
| compound I-J.15 | F | — | — | — |
| compound I-J.16 | — | F | — | — |
| compound I-J.17 | — | — | F | — |
| compound I-J.18 | — | — | — | F |
| compound I-J.19 | F | — | F | — |
| compound I-J.20 | F | — | F | F |
| compound I-J.21 | — | — | F | F |
| compound I-J.22 | Br | — | — | — |
| compound I-J.23 | — | Br | — | — |
| compound I-J.24 | — | — | Br | — |
| compound I-J.25 | — | — | — | Br |
| compound I-J.26 | Br | — | Br | — |
| compound I-J.27 | Br | — | Br | Br |
| compound I-J.28 | — | — | Br | Br |
| compound I-J.29 | $CF_3$ | — | — | — |
| compound I-J.30 | — | $CF_3$ | — | — |
| compound I-J.31 | — | — | $CF_3$ | — |
| compound I-J.32 | — | — | — | $CF_3$ |
| compound I-J.33 | $CF_3$ | — | $CF_3$ | — |
| compound I-J.34 | $CF_3$ | — | $CF_3$ | $CF_3$ |
| compound I-J.35 | — | — | $CF_3$ | $CF_3$ |
| compound I-J.36 | $OCF_3$ | — | — | — |
| compound I-J.37 | — | $OCF_3$ | — | — |
| compound I-J.38 | — | — | $OCF_3$ | — |
| compound I-J.39 | — | — | — | $OCF_3$ |
| compound I-J.40 | $OCF_3$ | — | $OCF_3$ | — |
| compound I-J.41 | $OCF_3$ | — | $OCF_3$ | $OCF_3$ |
| compound I-J.42 | — | — | $OCF_3$ | $OCF_3$ |
| compound I-J.43 | $CH_3$ | — | Cl | — |
| compound I-J.44 | Cl | — | $CH_3$ | — |
| compound I-J.45 | $CH_3$ | — | F | — |
| compound I-J.46 | F | — | $CH_3$ | — |

TABLE J-continued

|  | [R₂]ₘ | | | |
|---|---|---|---|---|
| Position of R₂: | A | B | C | D |
| compound I-J.47 | CH₃ | — | Br | — |
| compound I-J.48 | Br | — | CH₃ | — |
| compound I-J.49 | CH₃ | — | CF₃ | — |
| compound I-J.50 | CF₃ | — | CH₃ | — |
| compound I-J.51 | CH₃ | — | OCF₃ | — |
| compound I-J.52 | OCF₃ | — | CH₃ | — |
| compound I-J.53 | Cl | — | F | — |
| compound I-J.54 | F | — | Cl | — |
| compound I-J.55 | Cl | — | Br | — |
| compound I-J.56 | Br | — | Cl | — |
| compound I-J.57 | Cl | — | CF₃ | — |
| compound I-J.58 | CF₃ | — | Cl | — |
| compound I-J.59 | Cl | — | OCF₃ | — |
| compound I-J.60 | OCF₃ | — | Cl | — |
| compound I-J.61 | F | — | Br | — |
| compound I-J.62 | Br | — | F | — |
| compound I-J.63 | F | — | CF₃ | — |
| compound I-J.64 | CF₃ | — | F | — |
| compound I-J.65 | F | — | OCF₃ | — |
| compound I-J.66 | OCF₃ | — | F | — |
| compound I-J.67 | Br | — | CF₃ | — |
| compound I-J.68 | CF₃ | — | Br | — |
| compound I-J.69 | Br | — | OCF₃ | — |
| compound I-J.70 | OCF₃ | — | Br | — |
| compound I-J.71 | CF₃ | — | OCF₃ | — |
| compound I-J.72 | OCF₃ | — | CF₃ | — |

11. Formula I-K

Amongst compounds of the formula I, preference is given to the following compounds of the formula I-K, wherein n=2, $R^1=H_3C$ and X=S:

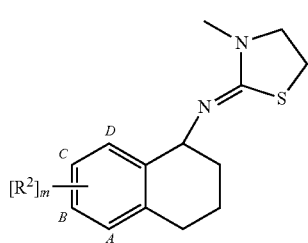

(I-K)

wherein the variables m and $R^2$ have the meanings given below. Examples of these compounds are those where $[R^2]_m$ has the meaning given in each line of table K (Compounds I-K.1 to I-K.72).

TABLE K

|  | [R₂]ₘ | | | |
|---|---|---|---|---|
| Position of R₂: | A | B | C | D |
| compound I-K.1 | CH₃ | — | — | — |
| compound I-K.2 | — | CH₃ | — | — |
| compound I-K.3 | — | — | CH₃ | — |
| compound I-K.4 | — | — | — | CH₃ |
| compound I-K.5 | CH₃ | — | CH₃ | — |
| compound I-K.6 | CH₃ | — | CH₃ | CH₃ |
| compound I-K.7 | — | — | CH₃ | CH₃ |
| compound I-K.8 | Cl | — | — | — |
| compound I-K.9 | — | Cl | — | — |
| compound I-K.10 | — | — | Cl | — |
| compound I-K.11 | — | — | — | Cl |
| compound I-K.12 | Cl | — | Cl | — |
| compound I-K.13 | Cl | — | Cl | Cl |
| compound I-K.14 | — | — | Cl | Cl |
| compound I-K.15 | F | — | — | — |
| compound I-K.16 | — | F | — | — |
| compound I-K.17 | — | — | F | — |
| compound I-K.18 | — | — | — | F |
| compound I-K.19 | F | — | F | — |
| compound I-K.20 | F | — | F | F |
| compound I-K.21 | — | — | F | F |
| compound I-K.22 | Br | — | — | — |
| compound I-K.23 | — | Br | — | — |
| compound I-K.24 | — | — | Br | — |
| compound I-K.25 | — | — | — | Br |
| compound I-K.26 | Br | — | Br | — |
| compound I-K.27 | Br | — | Br | Br |
| compound I-K.28 | — | — | Br | Br |
| compound I-K.29 | CF₃ | — | — | — |
| compound I-K.30 | — | CF₃ | — | — |
| compound I-K.31 | — | — | CF₃ | — |
| compound I-K.32 | — | — | — | CF₃ |
| compound I-K.33 | CF₃ | — | CF₃ | — |
| compound I-K.34 | CF₃ | — | CF₃ | CF₃ |
| compound I-K.35 | — | — | CF₃ | CF₃ |
| compound I-K.36 | OCF₃ | — | — | — |
| compound I-K.37 | — | OCF₃ | — | — |
| compound I-K.38 | — | — | OCF₃ | — |
| compound I-K.39 | — | — | — | OCF₃ |
| compound I-K.40 | OCF₃ | — | OCF₃ | — |
| compound I-K.41 | OCF₃ | — | OCF₃ | OCF₃ |
| compound I-K.42 | — | — | OCF₃ | OCF₃ |
| compound I-K.43 | CH₃ | — | Cl | — |
| compound I-K.44 | Cl | — | CH₃ | — |
| compound I-K.45 | CH₃ | — | F | — |
| compound I-K.46 | F | — | CH₃ | — |
| compound I-K.47 | CH₃ | — | Br | — |
| compound I-K.48 | Br | — | CH₃ | — |
| compound I-K.49 | CH₃ | — | CF₃ | — |
| compound I-K.50 | CF₃ | — | CH₃ | — |
| compound I-K.51 | CH₃ | — | OCF₃ | — |
| compound I-K.52 | OCF₃ | — | CH₃ | — |
| compound I-K.53 | Cl | — | F | — |
| compound I-K.54 | F | — | Cl | — |
| compound I-K.55 | Cl | — | Br | — |
| compound I-K.56 | Br | — | Cl | — |
| compound I-K.57 | Cl | — | CF₃ | — |
| compound I-K.58 | CF₃ | — | Cl | — |
| compound I-K.59 | Cl | — | OCF₃ | — |
| compound I-K.60 | OCF₃ | — | Cl | — |
| compound I-K.61 | F | — | Br | — |
| compound I-K.62 | Br | — | F | — |
| compound I-K.63 | F | — | CF₃ | — |
| compound I-K.64 | CF₃ | — | F | — |
| compound I-K.65 | F | — | OCF₃ | — |
| compound I-K.66 | OCF₃ | — | F | — |
| compound I-K.67 | Br | — | CF₃ | — |
| compound I-K.68 | CF₃ | — | Br | — |
| compound I-K.69 | Br | — | OCF₃ | — |
| compound I-K.70 | OCF₃ | — | Br | — |
| compound I-K.71 | CF₃ | — | OCF₃ | — |
| compound I-K.72 | OCF₃ | — | CF₃ | — |

12. Formula I-L

Amongst compounds of the formula I, preference is given to the following compounds of the formula I-L, wherein n=2, $R^1$=CN and X=S:

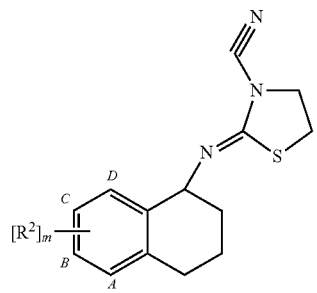

(I-L)

wherein the variables m and $R^2$ have the meanings given below. Examples of these compounds are those where $[R^2]_m$ has the meaning given in each line of table L (Compounds I-L.1 to I-L.72).

TABLE L

| Position of $R_2$: | A | B | C | D |
|---|---|---|---|---|
| | \multicolumn{4}{c}{$[R_2]_m$} |

| Position of $R_2$: | A | B | C | D |
|---|---|---|---|---|
| compound I-L.1 | CH$_3$ | — | — | — |
| compound I-L.2 | — | CH$_3$ | — | — |
| compound I-L.3 | — | — | CH$_3$ | — |
| compound I-L.4 | — | — | — | CH$_3$ |
| compound I-L.5 | CH$_3$ | — | CH$_3$ | — |
| compound I-L.6 | CH$_3$ | — | CH$_3$ | CH$_3$ |
| compound I-L.7 | — | — | CH$_3$ | CH$_3$ |
| compound I-L.8 | Cl | — | — | — |
| compound I-L.9 | — | Cl | — | — |
| compound I-L.10 | — | — | Cl | — |
| compound I-L.11 | — | — | — | Cl |
| compound I-L.12 | Cl | — | Cl | — |
| compound I-L.13 | Cl | — | Cl | Cl |
| compound I-L.14 | — | — | Cl | Cl |
| compound I-L.15 | F | — | — | — |
| compound I-L.16 | — | F | — | — |
| compound I-L.17 | — | — | F | — |
| compound I-L.18 | — | — | — | F |
| compound I-L.19 | F | — | F | — |
| compound I-L.20 | F | — | F | F |
| compound I-L.21 | — | — | F | F |
| compound I-L.22 | Br | — | — | — |
| compound I-L.23 | — | Br | — | — |
| compound I-L.24 | — | — | Br | — |
| compound I-L.25 | — | — | — | Br |
| compound I-L.26 | Br | — | Br | — |
| compound I-L.27 | Br | — | Br | Br |
| compound I-L.28 | — | — | Br | Br |
| compound I-L.29 | CF$_3$ | — | — | — |
| compound I-L.30 | — | CF$_3$ | — | — |
| compound I-L.31 | — | — | CF$_3$ | — |
| compound I-L.32 | — | — | — | CF$_3$ |
| compound I-L.33 | CF$_3$ | — | CF$_3$ | — |
| compound I-L.34 | CF$_3$ | — | CF$_3$ | CF$_3$ |
| compound I-L.35 | — | — | CF$_3$ | CF$_3$ |
| compound I-L.36 | OCF$_3$ | — | — | — |
| compound I-L.37 | — | OCF$_3$ | — | — |
| compound I-L.38 | — | — | OCF$_3$ | — |
| compound I-L.39 | — | — | — | OCF$_3$ |
| compound I-L.40 | OCF$_3$ | — | OCF$_3$ | — |
| compound I-L.41 | OCF$_3$ | — | OCF$_3$ | OCF$_3$ |
| compound I-L.42 | — | — | OCF$_3$ | OCF$_3$ |
| compound I-L.43 | CH$_3$ | — | Cl | — |
| compound I-L.44 | Cl | — | CH$_3$ | — |
| compound I-L.45 | CH$_3$ | — | F | — |
| compound I-L.46 | F | — | CH$_3$ | — |
| compound I-L.47 | CH$_3$ | — | Br | — |
| compound I-L.48 | Br | — | CH$_3$ | — |
| compound I-L.49 | CH$_3$ | — | CF$_3$ | — |
| compound I-L.50 | CF$_3$ | — | CH$_3$ | — |
| compound I-L.51 | CH$_3$ | — | OCF$_3$ | — |
| compound I-L.52 | OCF$_3$ | — | CH$_3$ | — |
| compound I-L.53 | Cl | — | F | — |
| compound I-L.54 | F | — | Cl | — |
| compound I-L.55 | Cl | — | Br | — |
| compound I-L.56 | Br | — | Cl | — |
| compound I-L.57 | Cl | — | CF$_3$ | — |
| compound I-L.58 | CF$_3$ | — | Cl | — |
| compound I-L.59 | Cl | — | OCF$_3$ | — |
| compound I-L.60 | OCF$_3$ | — | Cl | — |
| compound I-L.61 | F | — | Br | — |
| compound I-L.62 | Br | — | F | — |
| compound I-L.63 | F | — | CF$_3$ | — |
| compound I-L.64 | CF$_3$ | — | F | — |
| compound I-L.65 | F | — | OCF$_3$ | — |
| compound I-L.66 | OCF$_3$ | — | F | — |
| compound I-L.67 | Br | — | CF$_3$ | — |
| compound I-L.68 | CF$_3$ | — | Br | — |
| compound I-L.69 | Br | — | OCF$_3$ | — |
| compound I-L.70 | OCF$_3$ | — | Br | — |
| compound I-L.71 | CF$_3$ | — | OCF$_3$ | — |
| compound I-L.72 | OCF$_3$ | — | CF$_3$ | — |

Due to their excellent activity, the compounds of the formula I may be used for controlling animal pests, in particular selected harmful insects, arachnids and nematodes.

The compounds of the formula I and the pesticidal compositions comprising them are effective agents for controlling animal pests, selected from insects, arachnids and nematodes. Animal pests controlled by the compounds of formula I include for example:

Insects from the order of the lepidopterans (Lepidoptera), for example Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis;

beetles (Coleoptera), for example Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus and Sitophilus granaria;

dipterans (Diptera), for example Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea and Tipula paludosa;

thrips (Thysanoptera), e.g. Dichromothrips corbetti, Frankliniella fusca, Frankliniella occidentalis, Frankliniella tritici, Scirtothrips citri, Thrips oryzae, Thrips palmi and Thrips tabaci;

hymenopterans (Hymenoptera), e.g. Athalia rosae, Atta cephalotes, Atta sexdens, Atta texana, Hoplocampa minuta, Hoplocampa testudinea, Monomorium pharaonis, Solenopsis geminata and Solenopsis invicta;

heteropterans (Heteroptera), e.g. Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis and Thyanta perditor;

homopterans (Homoptera), e.g. Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand, and Viteus vitifolii;

termites (Isoptera), e.g. Calotermes flavicollis, Leucotermes flavipes, Reticulitermes flavipes, Reticulitermes lucifugus und Termes natalensis;

orthopterans (Orthoptera), e.g. Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus;

arachnoidea, such as arachnids (Acarina), e.g. of the families Argasidae, Ixodidae and Sarcoptidae, such as Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei, and Eriophyidae spp. such as Aculus schlechtendali, Phyllocoptrata oleivora and Eriophyes sheldoni; Tarsonemidae spp. such as Phytonemus pallidus and Polyphagotarsonemus latus; Tenuipalpidae spp. such as Brevipalpus phoenicis; Tetranychidae spp. such as Tetranychus cinnabarinus, Tetranychus kanzawai, Tetranychus pacificus, Tetranychus telarius and Tetranychus urticae, Panonychus ulmi, Panonychus citri, and oligonychus pratensis;

siphonatera, e.g. Xenopsylla cheopsis, Ceratophyllus spp.

The compositions and compounds of formula I are useful for the control of nematodes, especially plant parasitic nematodes such as root knot nematodes, Meloidogyne hapla, Meloidogyne incognita, Meloidogyne javanica, and other Meloidogyne species; cyst-forming nematodes, Globodera rostochiensis and other Globodera species; Heterodera avenae, Heterodera glycines, Heterodera schachtii, Heterodera trifolii, and other Heterodera species; Seed gall nematodes, Anguina species; Stem and foliar nematodes, Aphelenchoides species; Sting nematodes, Belonolaimus longicaudatus and other Belonolaimus species; Pine nematodes, Bursaphelenchus xylophilus and other Bursaphelenchus species; Ring nematodes, Criconema species, Criconemella species, Criconemoides species, Mesocriconema species; Stem and bulb nematodes, Ditylenchus destructor, Ditylenchus dipsaci and other Ditylenchus species; Awl nematodes, Dolichodorus species; Spiral nematodes, Heliocotylenchus multicinctus and other Helicotylenchus species; Sheath and sheathoid nematodes, Hemicycliophora species and Hemicriconemoides species; Hirshmanniella species; Lance nematodes, Hoploaimus species; false rootknot nematodes, Nacobbus species; Needle nematodes, Longidorus elongatus and other Longidorus species; Pin nematodes, Paratylenchus species; Lesion nematodes, Pratylenchus neglectus, Pratylenchus penetrans, Pratylenchus curvitatus, Pratylenchus goodeyi and other Pratylenchus species; Burrowing nematodes, Radopholus similis and other Radopholus species; Reniform nematodes, Rotylenchus robustus and other Rotylenchus species; Scutellonema species; Stubby root nematodes, Trichodorus primitivus and other Trichodorus species, Paratrichodorus species; Stunt nematodes, Tylenchorhynchus claytoni, Tylenchorhynchus dubius and other Tylenchorhynchus species; Citrus nematodes, Tylenchulus species; Dagger nematodes, Xiphinema species; and other plant parasitic nematode species.

In a preferred embodiment of the invention the compounds of formula I are used for controlling insects or arachnids, in particular insects of the orders *Lepidoptera, Coleoptera* and *Homoptera* and arachnids of the order Acarina. The compounds of the formula I according to the present invention are in particular useful for controlling insects of the order *Lepidoptera* and *Homoptera*.

Formulations

Accordingly, the invention further provides agriculturally compositions for combating such animal pests, which comprises such an amount of at least one compound of the formula I or at least an agriculturally useful salt of I and at least one inert liquid and/or solid agronomically acceptable carrier that it has a pesticidal action and, if desired, at least one surfactant.

Such a composition may contain a single active compound of the formula I or the enantiomers thereof or a mixture of several active compounds I according to the present invention. The composition according to the present invention may comprise an individual isomer or mixtures of isomers as well as individual tautomers or mixtures of tautomers.

For use in a method according to the present invention, the compounds I can be converted into the customary formulations, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of the formula I according to the present invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Solvents/carriers, which are suitable, are e.g.:
solvents such as water, aromatic solvents (for example Solvesso products, xylene and the like), paraffins (for example mineral fractions), alcohols (for example methanol, butanol, pentanol, benzyl alcohol), ketones (for example cyclohexanone, gamma-butyrolactone), pyrrolidones (N-methyl-pyrrolidone (NMP), N-octylpyrrolidone NOP), acetates (glycol diacetate), alkyl lactates, lactones such as g-butyrolactone, glycols, fatty acid dimethylamides, fatty acids and fatty acid esters, triglycerides, oils of vegetable or animal origin and modified oils such as alkylated plant oils. In principle, solvent mixtures may also be used.
carriers such as ground natural minerals and ground synthetic minerals, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example dichlorophen und benzyl alcohol hemiformal Suitable thickeners are compounds, which confer a pseudoplastic flow behavior to the formulation, i.e. high viscosity at rest and low viscosity in the agitated stage. Mention may be made, in this context, for example, of commercial thickeners based on polysaccharides, such as Xanthan Gum® (Kelzan® from Kelco), Rhodopol® 23 (Rhone Poulenc) or Veegum® (from R.T. Vanderbilt), or organic phyllosilicates, such as Attaclay® (from Engelhardt). Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof. Biocides can be added to stabilize the compositions according to the invention against attack by microorganisms. Suitable biocides are, for example, based on isothiazolones such as the compounds marketed under the trademarks Proxel® from Avecia (or Arch) or Acticide® RS from Thor Chemie and Kathon® MK from Rohm & Haas. Suitable antifreeze agents are organic polyols, for example ethylene glycol, propylene glycol or glycerol. These are usually employed in amounts of not more than 10% by weight, based on the total weight of the active compound composition. If appropriate, the active compound compositions according to the invention may comprise 1 to 5% by weight of buffer, based on the total amount of the formulation prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient(s). The active ingredient(s) are employed in a purity of from 90% to 100%, preferably 95% to 100% (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compound of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1% per weight.

The active ingredients may also be used successfully in the ultra-low-volume process (ULV), it being possible to apply formulations comprising over 95% by weight of active ingredient, or even to apply the active ingredient without additives.

The following are examples of formulations:

1. Products for dilution with water. For seed treatment purposes, such products may be applied to the seed diluted or undiluted.

A) Water-Soluable Concentrates (SL, LS)

10 parts by weight of the active compound is dissolved in 90 parts by weight of water or a water-soluable solvent. As an alternative, wetters or other auxiliaries are added. The active compound dissolves upon dilution with water, whereby a formulation with 10% (w/w) of active compound is obtained.

B) Dispersible Concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.

C) Emulsifiable Concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions (EW, EO, ES)

25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions (SC, OD, FS)

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-Dispersible Granules and Water-Soluable Granules (WG, SG)

50 parts by weight of the active compound is ground finely with addition of 50 parts by weight of dispersants and wetters and made as water-dispersible or water-soluable granules by means of technical appliances (for example extrusion, spray tower, fluidized bed). Dilution with water gives a stable dispersion or solution of the active compound, whereby a formulation with 50% (w/w) of active compound is obtained.

G) Water-Dispersible Powders and Water-Soluable Powders (WP, SP, SS, WS)

75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders (DP, DS)

5 parts by weight of the active compound are ground finely and mixed intimately with 95 parts by weight of finely divided kaolin. This gives a dustable product having 5% (w/w) of active compound.

J) Granules (GR, FG, GG, MG)

0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV Solutions (UL)

10 parts by weight of the active compound is dissolved in 90 parts by weight of an organic solvent, for example xylene. This gives a product having 10% (w/w) of active compound, which is applied undiluted for foliar use.

Various types of oils, wetters, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds and compositions of the present invention compounds I may be applied with other active ingredients, for example with other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These additional active agents can be admixed with the agents used according to the invention in a weight ratio of 1:10 to 10:1. Mixing the compounds I, or the compositions comprising them in the use form as pesticides with other pesticides frequently results in a broader pesticidal spectrum of action The following list M of pesticides together with which the compounds according to the invention can be used and with which potential synergistic effects might be produced, is intended to illustrate the possible combinations, but not to impose any limitation:

M.1. Organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

M.2. Carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

M.3. Pyrethroids: allethrin, bifenthrin, cyfluthrin, cyhalothrin, cyphenothrin, cypermethrin, alpha-cypermethrin, beta-cypermethrin, zeta-cypermethrin, deltamethrin, empenthrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

M.4. Growth regulators: a) chitin synthesis inhibitors: benzoylureas: chlorfluazuron, diflubenzuron, flucycloxuron, flufenoxuron, hexaflumuron, lufenuron, novaluron, tebufenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

M.5. Nicotinic receptor agonists/antagonists compounds: clothianidin, dinotefuran, imidacloprid, thiamethoxam, nitenpyram, acetamiprid, thiacloprid and AKD-1022;

M.6. GABA antagonist compounds: acetoprole, endosulfan, ethiprole, fipronil, vaniliprole, pyrafluprole, pyriprole, the phenylpyrazole compound of formula I⁻²

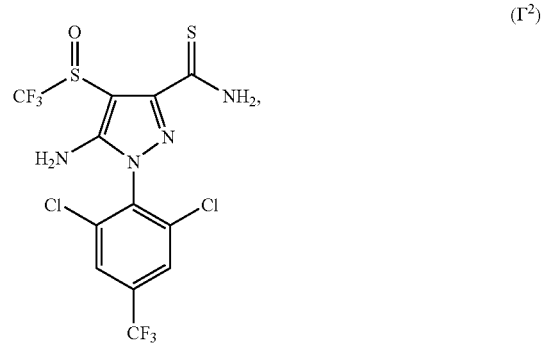

(I⁻²)

M.7. Macrocyclic lactone insecticides: abamectin, emamectin, milbemectin, lepimectin, spinosad M.8. METI I compounds: fenazaquin, pyridaben, tebufenpyrad, tolfenpyrad, flufenerim;

M.9. METI II and III compounds: acequinocyl, fluacyprim, hydramethylnon;

M.10. Uncoupler compounds: chlorfenapyr;

M.11. Oxidative phosphorylation inhibitor compounds: cyhexatin, diafenthiuron, fenbutatin oxide, propargite;

M.12. Moulting disruptor compounds: cyromazine;

M.13. Mixed Function Oxidase inhibitor compounds: piperonyl butoxide;

M.14. Sodium channel blocker compounds: indoxacarb, metaflumizone,

M.15. Various: amitraz, benclothiaz, bifenazate, cartap, flonicamid, pyridalyl, pymetrozine, sulfur, thiocyclam, flubendiamide, cyenopyrafen, flupyrazofos, cyflumetofen, amidoflumet, pyrifluquinazon, the aminoquinazolinone compound of formula I⁻⁴

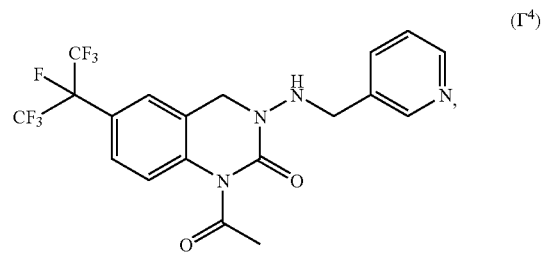

(I⁻⁴)

N—R'-2,2-dihalo-1-R"cyclo-propanecarboxamide-2-(2, 6-dichloro-α,α,α-tri-fluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, anthranilamide compounds as chlorantraniliprole or the compound of formula I'⁵

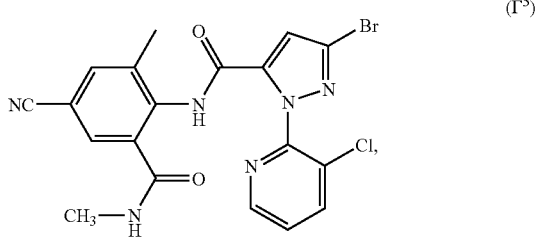

and malononitrile compounds as described in JP 2002 284608, WO 02/89579, WO 02/90320, WO 02/90321, WO 04/06677, WO 04/20399, JP 2004 99597, WO 05/68423, WO 05/68432, or WO 05/63694, especially the malononitrile compounds $CF_3(CH_2)_2C(CN)_2CH_2(CF_2)_3CF_2H$, $CF_3(CH_2)_2 C(CN)_2CH_2(CF_2)_5CF_2H$, $CF_3(CH_2)_2C(CN)_2(CH_2)_2C(CF_3)_2 F$, $CF_3(CH_2)_2C(CN)_2(CH_2)_2(CF_2)_3CF_3$, $CF_2H(CF_2)_3 CH_2C(CN)_2CH_2(CF_2)_3CF_2H$, $CF_3(CH_2)_2C(CN)_2CH_2 (CF_2)_3 CF_3$, $CF_3(CF_2)_2CH_2C(CN)_2CH_2(CF_2)_3CF_2H$, and $CF_3CF_2CH_2C(CN)_2CH_2(CF_2)_3CF_2H$.

The commercially available compounds of the group M may be found in The Pesticide Manual, 13$^{th}$ Edition, British Crop Protection Council (2003) among other publications. Thioamides of formula I'² and their preparation have been described in WO 98/28279. Lepimectin is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1 462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. Cyflumetofen and its preparation have been described in WO 04/080180. The aminoquinazolinone compound of formula I'⁴ has been described in EP A 109 7932.

Anthranilamides of formula I'⁵ and their preparation have been described in WO 01/70671; WO 02/48137; WO 03/24222, WO 03/15518, WO 04/67528; WO 04/33468; and WO 05/118552. The malononitrile compounds $CF_3(CH_2)_2C(CN)_2CH_2(CF_2)_3CF_2H$, $CF_3(CH_2)_2C(CN)_2CH_2(CF_2)_5 CF_2H$, $CF_3(CH_2)_2C(CN)_2(CH_2)_2C(CF_3)_2F$, $CF_3(CH_2)_2C(CN)_2(CH_2)_2(CF_2)_3CF_3$, $CF_2H(CF_2)_3CH_2C(CN)_2CH_2(CF_2)_3CF_2H$, $CF_3(CH_2)_2C(CN)_2CH_2(CF_2)_3CF_3$, $CF_3(CF_2)_2 cH_2C(CN)_2CH_2(CF_2)_3CF_2H$, and $CF_3CF_2CH_2C(CN)_2CH_2 (CF_2)_3 CF_2H$ have been described in WO 05/63694.

Fungicidal mixing partners are those selected from the group F consisting of

F.1 acylalanines such as benalaxyl, metalaxyl, ofurace, oxadixyl;

F.2 amine derivatives such as aldimorph, dodine, dodemorph, fenpropimorph, fenpropidin, guazatine, iminoctadine, spiroxamin, tridemorph;

F.3 anilinopyrimidines such as pyrimethanil, mepanipyrim or cyrodinyl;

F.4 antibiotics such as cycloheximid, griseofulvin, kasugamycin, natamycin, polyoxin or streptomycin;

F.5 azoles such as bitertanol, bromoconazole, cyproconazole, difenoconazole, dinitroconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol;

F.6 dicarboximides such as iprodion, myclozolin, procymidon, vinclozolin;

F.7 dithiocarbamates such as ferbam, nabam, maneb, mancozeb, metam, metiram, propineb, polycarbamate, thiram, ziram, zineb;

F.8 heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine;

F.9 copper fungicides such as Bordeaux mixture, copper acetate, copper oxychloride, basic copper sulfate;

F.10 nitrophenyl derivatives such as binapacryl, dinocap, dinobuton, nitrophthalisopropyl;

F.11 phenylpyrroles such as fenpiclonil or fludioxonil;

F.12 strobilurins such as azoxystrobin, dimoxystrobin, fluoxastrobin, kresoxim-methyl, metominostrobin, orysastrobin, picoxystrobin or trifloxystrobin;

F.13 sulfenic acid derivatives such as captafol, captan, dichlofluanid, folpet, tolylfluanid;

F.14 cinnemamides and analogs such as dimethomorph, flumetover or flumorph;

F.15 sulfur, and other fungicides such as acibenzolar-5-methyl, benthiavalicarb, carpropamid, chlorothalonil, cyflufenamid, cymoxanil, dazomet, diclomezin, diclocymet, diethofencarb, edifenphos, ethaboxam, fenhexamid, fentinacetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid.

Applications

The animal pest, i.e. the insects, arachnids and nematodes, the plant, soil or water in which the plant is growing can be contacted with the present compound(s) I or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of formula I or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

Moreover, animal pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

The compounds of the invention can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formula I are effective through both contact (via soil, glass, wall, bed net, carpet, plant parts or animal parts), and ingestion (bait, or plant part).

For use against ants, termites, wasps, flies, mosquitos, crickets, or cockroaches, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formula I as aerosols (e.g. in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulphoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formula I and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethyl-cyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of formula I and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient is from 0.001 weight % to 15 weight %, desirably from 0.001 weight % to 5% weight % of active compound.

For use in spray compositions, the content of active ingredient is from 0.001 to 80 weights %, preferably from 0.01 to 50 weight % and most preferably from 0.01 to 15 weight %.

For use in treating crop plants, the rate of application of the active ingredients of this invention may be in the range of 0.1 g to 4000 g per hectare, desirably from 25 g to 600 g per hectare, more desirably from 50 g to 500 g per hectare.

Seed Treatment

The compounds of formula I are also suitable for the treatment of seeds in order to protect the seed from insect pest, in particular from soil-living insect pests and the resulting plant's roots and shoots against soil pests and foliar insects.

The compounds of formula I are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the general formula I or a salt thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing Bacillus thuringiensis toxins (Bt toxins) which make the plants resistant to certain pests (EP-A-0142924, EP-A-0193259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:

A Soluable concentrates (SL, LS)
D Emulsions (EW, EO, ES)
E Suspensions (SC, OD, FS)
F Water-dispersible granules and water-soluable granules (WG, SG)
G Water-dispersible powders and water-soluable powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluable powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of formula I for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

In the treatment of seed, the application rates of the compounds I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed. For specific crops such as lettuce the rate can be higher.

The invention therefore also relates to seed comprising a compound of the formula I, or an agriculturally useful salt of 1, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed.

Animal Health

The compounds of formula I or the enantiomers or veterinarily acceptable salts thereof are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula I or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula I or the enantiomers or veterinarily acceptable salts thereof or a composition comprising it.

The invention also provides a process for the preparation of a composition for treating, controlling, preventing or protecting animals against infestation or infection by parasites which comprises a parasiticidally effective amount of a compound of formula I or the enantiomers or veterinarily acceptable salts thereof or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula I are suitable for combating endo- and ectoparasites in and on animals.

Compounds of formula I or the enantiomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I or the enantiomers or veterinarily acceptable salts thereof and compositions comprising them are suitable for systemic and/or non-systemic control of ecto- and/or endoparasites. They are active against all or some stages of development.

The compounds of formula I are especially useful for combating ectoparasites.

The compounds of formula I are especially useful for combating parasites of the following orders and species, respectively:

fleas (*Siphonaptera*), e.g. *Ctenocephalides felis, Ctenocephalides canis, Xenopsylla cheopis, Pulex irritans, Tunga penetrans*, and *Nosopsyllus fasciatus*, cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (*Diptera*), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides,*

*Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis,* lice (*Phthiraptera*), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.* ticks and parasitic mites (Parasitiformes): ticks (*Ixodida*), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (*Mesostigmata*), e.g. *Ornithonyssus bacoti* and *Dermanyssus gallinae,*

Actinedida (*Prostigmata*) und Acaridida (*Astigmata*) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (*Heteropterida*): *Cimex lectularius, Cimex hemipterus, Reduvius senilis, Triatoma* spp., *Rhodnius* ssp., *Panstrongylus* ssp. and *Arilus critatus, Anoplurida,* e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi,* and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, *Cercomeromorpha,* in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula I and compositions containing them are particularly useful for the control of pests from the orders *Diptera, Siphonaptera* and *Ixodida.*

Moreover, the use of the compounds of formula I and compositions containing them for combating mosquitoes is especially preferred.

The use of the compounds of formula I and compositions containing them for combating flies is a further preferred embodiment of the present invention.

Furthermore, the use of the compounds of formula I and compositions containing them for combating fleas is especially preferred.

The use of the compounds of formula I and compositions containing them for combating ticks is a further preferred embodiment of the present invention.

The compounds of formula I also are especially useful for combating endoparasites (roundworms nematoda, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraluminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-diox-olane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:

liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:

non-ionic surfactants, e.g. polyethoxylated castor oil, polyethoxylated sorbitan monooleate, sorbitan monostearate, glycerol monostearate, polyoxyethyl stearate, alkylphenol polyglycol ether;

ampholytic surfactants such as di-sodium N-lauryl-p-iminodipropionate or lecithin; anionic surfactants, such as sodium lauryl sulfate, fatty alcohol ether sulfates, mono/dialkyl polyglycol ether orthophosphoric acid ester monoethanolamine salt; cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formula I.

Generally it is favorable to apply the compounds of formula I in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formula I them are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

The present invention is now illustrated in further detail by the following examples.

P. PREPARATION EXAMPLES

Example P.1

(4-Chloro-indan-1-yl)-(4,5-dihydrothiazol-2-yl)-amine (Compound Example 4 of Table 1)

To a solution of 4-chloro-indan-1-ylamine (390 mg) in diethyl ether (20 ml) was added 1-chloro-2-isothiocyanatoethane (283 mg) at 0° C. and the solution stirred for 2 h at the same temperature. The reaction mixture was quenched with diluted sodium hydroxide solution and extracted with diethyl ether. The residue was purified on silica gel to yield 240 mg of the product (41%).

Example P.2

(7-Chloro-1,2,3,4-tetrahydro-naphthalen-1-yl)-(4,5-dihydro-thiazol-2-yl)-amine (Compound Example 9 of Table 1)

To a solution of 7-chloro-1,2,3,4-tetrahydro-naphthalen-1-ylamine (200 mg) in diethyl ether (5 ml) was added a solution of 1-chloro-2-isothiocyanatoethane (134 mg) in diethyl ether (5 ml) at 0° C. and the solution stirred for 4 h at the same temperature. The reaction mixture was quenched with diluted sodium hydroxide solution and extracted with diethyl ether. The residue was purified on silica gel to yield 171 mg of the product (52%).

C. Compound Examples of Formula I:

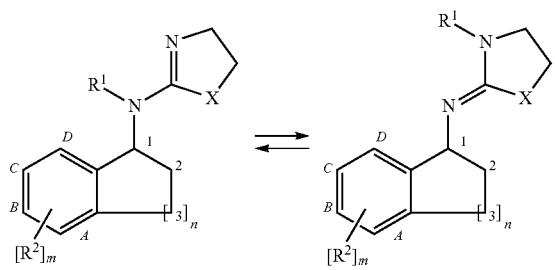

TABLE 1

| Ex. | n | $R^1$ | A | B | C | D | X | Physico-chemical data (melting point [° C.]) |
|---|---|---|---|---|---|---|---|---|
| | | | | $[R^2]_m$ | | | | |
| 1 | 1 | H | | | Cl | | S | 163-164 |
| 2 | 1 | H | | | F | | S | 146-147 |
| 3 | 1 | H | | | Br | | S | 168-169 |
| 4 | 1 | H | Cl | | | | S | 171-175 |
| 5 | 1 | H | Cl | | Cl | | S | 137-139 |
| 6 | 1 | H | F | | F | | S | 136-139 |
| 7 | 2 | H | Cl | | Cl | | S | 160-162 |
| 8 | 2 | H | | | Br | | S | 161-163 |
| 9 | 2 | H | | | Cl | | S | 168-171 |
| 10 | 1 | H | $CH_3$ | | | | S | 122-127 |
| 11 | 2 | H | Br | | | | S | 174-179 |
| 12 | 1 | H | | | $OCH_3$ | | S | 143-145 |
| 13 | 1 | H | F | | | | S | 137-141 |
| 14 | 1 | H | $OCH_3$ | | | | S | 126-128 |
| 15 | 1 | H | | | $CH_3$ | | S | 180-182 |
| 16 | 1 | H | CN | | | | S | 121-124 |
| 17 | 1 | H | | | $CO_2CH_3$ | | S | 204-206 |
| 18 | 1 | H | | CN | | | S | 175-180 |
| 19 | 1 | H | | | | Cl | S | 128-130 |
| 20 | 1 | H | $CH_3$ | | | $CH_3$ | S | 130-136 |
| 21 | 1 | H | $CH_3$ | | $CH_3$ | | S | 165-169 |
| 22 | 1 | H | $CH_3$ | $CH_3$ | | | S | 166-168 |
| 23 | 1 | H | | $CO_2CH_3$ | | | S | 185-191 |
| 24 | 1 | H | F | | | | S | 137-138 |
| 25 | 1 | H | | | $SCH_3$ | | S | 144-146 |
| 26 | 1 | H | | Cl | $OCH_3$ | | S | 175-177 |
| 27 | 1 | H | | | | CN | S | 172-175 |

B. Examples of Action Against Pests

The action of the compounds I against pests was demonstrated by the following experiments:

B.1 Cotton Aphid (*Aphis gossypii*)

Cotton plants in the cotyledon stage (variety 'Delta Pine') are infested with approximately 100 laboratory-reared aphids by placing infested leaf sections on top of the test plants. The leaf sections are removed after 24 hr. The cotyledons of the intact plants are dipped into gradient solutions of the test compound. Aphid mortality on the treated plants, relative to mortality on check plants, is determined after 5 days.

In this test, compound examples nos 1-6, 9, 12, 13, 15, 21 and 24 at 300 ppm showed over 80% mortality in comparison with untreated controls.

B.2 Green Peach Aphid (*Myzus persicae*)

Pepper plants in the 2nd leaf-pair stage (variety 'California Wonder') are infested with approximately 40 laboratory-reared aphids by placing infested leaf sections on top of the test plants. The leaf sections are removed after 24 hr. The leaves of the intact plants are dipped into gradient solutions of the test compound. Aphid mortality on the treated plants, relative to mortality on check plants, is determined after 5 days.

In this test, compound examples nos 1-6, 9, 10, 12, 13, 15, 20, 21 and 24 at 300 ppm showed over 80% mortality in comparison with untreated controls.

The invention claimed is:

1. A tautomeric Indanyl- or Tetrahydronaphthyl-amino-azoline compound of the formula I

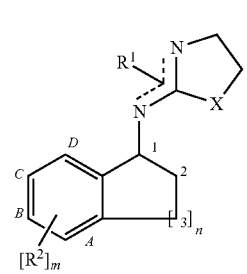

formula I wherein n is 1 or 2;

m is 1, 2, 3 or 4, wherein when m is greater than 1, the radicals $R^2$ may have the same or different meanings X is O, S, $NR^3$ wherein $R^3$ is selected from hydrogen, cyano, nitro, formyl, C(=O)$R^{3c}$, $C_1$-$C_6$-alkyl, $C_2$-$C_6$-alkenyl, $C_2$-$C_6$-alkynyl, $C_3$-$C_8$-cycloalkyl, $C_1$-$C_6$-alkoxy, $C_2$-$C_6$-alkynylamino, di($C_2$-$C_6$-alkynyl)amino, ($C_1$-$C_6$-alkoxy)methylene, $C_1$-$C_6$-alkylsulfinyl, $C_1$-$C_6$-alkylsulfenyl or $C_1$-$C_6$-alkylsulfonyl wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, or C(O)$NR^{3a}R^{3b}$, (SO2)$NR^{3a}R^{3b}$, phenyl, phenyloxy or benzyl, each of the last three mentioned radicals may be unsubstituted or substituted with 1 to 5 radicals, independently of one another selected from the group consisting of halogen, $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy and $C_1$-$C_6$-haloalkoxy; and wherein $R^{3a}$ and $R^{3b}$ are each independently hydrogen, $C_1$-$C_6$-alkyl, $C_1$-$C_6$-haloalkyl, $C_2$-$C_6$-alkenyl, or $C_2$-$C_6$-alkynyl;

$R^{3c}$ is selected from hydrogen, $C_1$-$C_6$-alkyl, $C_2$-$C_6$-alkenyl, $C_2$-$C_6$-alkynyl, $C_3$-$C_8$-cycloalkyl, $C_1$-$C_6$-alkylthio, $C_1$-$C_6$-alkoxy, ($C_1$-$C_6$-alkyl)amino, di($C_1$-$C_6$-alkyl)amino, phenyl and heteroaryl, which can be a mono- or bicyclic 5 to 10 membered heteroaromatic ring, which contains 1, 2, 3 or 4 heteroatoms selected from O, S and N;

$R^1$ is selected from hydrogen, cyano, nitro, formyl, C(=O)$R^{1c}$, $C_1$-$C_6$-alkyl, $C_2$-$C_6$-alkenyl, $C_2$-$C_6$-alkynyl, $C_3$-$C_8$-cycloalkyl, $C_1$-$C_6$-alkoxy, ($C_1$-$C_6$-alkoxy)methylene, $C_1$-$C_6$-alkylsulfinyl, $C_1$-$C_6$-alkylsulfenyl or $C_1$-$C_6$-alkylsulfonyl wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, or $C(O)NR^{1a}R^{1b}$, $(SO2)NR^{1a}R^{1b}$, phenyl, phenyloxy or benzyl, each of the last three mentioned radicals may be unsubstituted or substituted with 1 to 5 radicals, independently of one another selected from the group consisting of halogen, $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy and $C_1$-$C_6$-haloalkoxy; and wherein $R^{1a}$ and $R^{1b}$ are each independently hydrogen, $C_1$-$C_6$-alkyl, $C_1$-$C_6$-haloalkyl, $C_2$-$C_6$-alkenyl, or $C_2$-$C_6$-alkynyl.

$R^{1c}$ is selected from hydrogen, $C_1$-$C_6$-alkyl, $C_2$-$C_6$-alkenyl, $C_2$-$C_6$-alkynyl, $C_3$-$C_8$-cycloalkyl, $C_1$-$C_6$-alkylthio, $C_1$-$C_6$-alkoxy, ($C_1$-$C_6$-alkyl)amino, di($C_1$-$C_6$-alkyl)amino, phenyl and heteroaryl, which can be a mono- or bicyclic 5 to 10 membered heteroaromatic ring, which contains 1, 2, 3 or 4 heteroatoms selected from O, S and N;

$R^2$ is selected from halogen, OH, SH, $NH_2$, $SO_3H$, COOH, cyano, azido, nitro, formyl, $CONH_2$, $CSNH_2$, CH=N—OH, CH=N—O—($C_1$-$C_6$)-alkyl, C(=O)$R^{2c}$, C(=S)$R^{2c}$, $C_1$-$C_6$-haloalkyl, $C_2$-$C_6$-alkenyl, $C_2$-$C_6$-alkynyl, $C_3$-$C_8$-cycloalkyl, $C_1$-$C_6$-alkoxy, $C_1$-$C_6$-alkylamino, di($C_1$-$C_6$-alkyl)amino, $C_1$-$C_8$-alkylthio, $C_2$-$C_6$-alkenyloxy, $C_2$-$C_6$-alkenylamino, $C_2$-$C_6$-alkenylthio, $C_2$-$C_6$-alkynyl, $C_2$-$C_6$-alkynyloxy, $C_2$-$C_6$-alkynylamino, $C_2$-$C_6$-alkynylthio, $C_1$-$C_6$-alkylsulfonyl, $C_1$-$C_6$-alkylsulfoxyl, $C_2$-$C_6$-alkenylsulfonyl, $C_2$-$C_6$-alkynylsulfonyl, ($C_1$-$C_6$-alkoxy)carbonyl, ($C_2$-$C_6$-alkenyloxy)carbonyl, ($C_2$-$C_6$-alkynyloxy)-carbonyl, ($C_1$-$C_6$-alkyl)carbonyloxy, ($C_2$-$C_6$-alkenyl)carbonyl-oxy or ($C_2$-$C_6$-alkynyl-)carbonyloxy, ($C_2$-$C_6$-alkenyl)carbonyl-amino, wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio; $C(O)NR^{2a}R^{2b}$, $(SO_2)NR^{2a}R^{2b}$, wherein $R^{2a}$ and $R^{2b}$ are each independently selected from hydrogen, OH, $NH_2$, $C_1$-$C_6$-alkyl, $C_1$-$C_6$-haloalkyl, $C_2$-$C_6$-alkenyl or $C_2$-$C_6$-alkynyl.

$R^{2c}$ is selected from hydrogen, $C_1$-$C_6$-alkyl, $C_2$-$C_6$-alkenyl, $C_2$-$C_6$-alkynyl, $C_3$-$C_8$-cycloalkyl, $C_1$-$C_6$-alkoxy, ($C_1$-$C_6$-alkyl)amino, di($C_1$-$C_6$-alkyl)amino, hydrazino, ($C_1$-$C_6$-alkyl)hydrazino, di($C_1$-$C_6$-alkyl)hydrazino, phenyl and heteroaryl, which can be a mono- or bicyclic 5 to 10 membered heteroaromatic ring, which contains 1, 2, 3 or 4 heteroatoms selected from O, S and N;

a radical Y—Ar or a radical Y-Cy, wherein

Y is a single bond, oxygen, sulfur, nitrogen, $C_1$-$C_6$-alkandiyl or $C_1$-$C_6$-alkandiyloxy;

Ar is phenyl, naphthyl or a mono- or bicyclic 5- to 10-membered heteroaromatic ring, which contains 1, 2, 3 or 4 heteroatoms selected from two oxygen, two sulfur and three nitrogen atoms as ring members, wherein Ar is unsubstituted or may carry any combination of 1 to 5 radicals, independently of one another selected from the group consisting of halogen, cyano, nitro, hydroxy, mercapto, amino, carboxyl, $C_1$-$C_6$-alkyl, $C_1$-$C_6$-haloalkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

Cy is $C_3$-$C_{12}$-cycloalkyl, which is unsubstituted or substituted with 1 to 5 radicals, independently of one another selected from the group consisting of halogen, cyano, nitro, hydroxy, mercapto, amino, carboxyl, $C_1$-$C_6$-alkyl, $C_1$-$C_6$-haloalkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

and wherein the radical $R^2$ that are bound to adjacent carbon atoms of the phenyl rings may form, together with said carbon atoms, a fused benzene ring, a fused saturated or partially unsaturated 5-, 6-, or 7-membered carbocycle or a fused 5-, 6- or 7-membered heterocycle, which contains 1, 2, 3 or 4 heteroatoms selected from 2 oxygen, 2 sulfur and 3 nitrogen atoms as ring members, and wherein the fused ring is unsubstituted or may carry 1, 2, 3 or 4 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

or the enantiomers and/or the agriculturally and/or veterinary acceptable salts thereof, with the proviso that compound of formula I is not 2-(4-thio-tert-butyl-1-indanylamino)-oxazoline, wherein the compound of formula I is pesticidally effective for the protection of growing plants and crops from attack or infestation by animal pests.

2. The Indanyl- or Tetrahydronaphthyl-amino-azoline compound of formula I, according to claim 1, wherein $R^1$ is selected from hydrogen, cyano, C(=O)$R^{1c}$, $C_1$-$C_6$-alkyl, $C_2$-$C_6$-alkenyl, $C_2$-$C_6$-alkynyl, $C_3$-$C_8$-cycloalkyl, $C_1$-$C_6$-alkoxy, and wherein $R^{1c}$ is selected from hydrogen, $C_1$-$C_6$-alkyl, $C_2$-$C_6$-alkenyl, $C_2$-$C_6$-alkynyl, $C_3$-$C_8$-cycloalkyl, $C_1$-$C_6$-alkoxy, ($C_1$-$C_6$-alkyl)amino, di($C_1$-$C_6$-alkyl)amino, phenyl and heteroaryl, which can be a mono- or bicyclic 5 to 10 membered heteroaromatic ring, which contains 1, 2, 3 or 4 heteroatoms selected from O, S and N.

3. The Indanyl- or Tetrahydronaphthyl-amino-azoline compound of formula I according to claim 1, wherein $R^1$ is hydrogen.

4. The Indanyl- or Tetrahydronaphthyl-amino-azoline compound of formula I according to claim 1, wherein $R^2$ is selected from cyano, azido, halogen, OH, SH, $NH_2$, $CONH_2$, $SO_3H$, COOH, C(=O)$R^{2c}$, $C_1$-$C_6$-haloalkyl, $C_2$-$C_6$-alkenyl, $C_2$-$C_6$-alkynyl, $C_3$-$C_8$-cycloalkyl, $C_1$-$C_6$-alkoxy, ($C_1$-$C_6$-alkyl)amino, di($C_1$-$C_6$-alkyl)amino, wherein the carbon atoms in the aliphatic radicals of the aforementioned groups may carry any combination of 1, 2 or 3 radicals, independently of one another selected from the group consisting of halogen, cyano, nitro, hydroxy, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and wherein $R^{2c}$ is selected from hydrogen, $C_1$-$C_6$-alkyl, $C_2$-$C_6$-alkenyl, $C_2$-$C_6$-alkynyl, $C_3$-$C_s$-cycloalkyl, $C_1$-$C_6$-alkoxy, ($C_1$-$C_6$-alkyl)amino, di($C_1$-$C_6$-alkyl)amino, phenyl and heteroaryl, which can be a mono- or bicyclic 5 to 10 membered heteroaromatic ring, which contains 1, 2, 3 or 4 heteroatoms selected from O, S and N.

5. The Indanyl- or Tetrahydronaphthyl-amino-azoline compound of formula I according to claim 1, wherein
R$^2$ is selected from halogen, $C_1$-$C_6$-haloalkyl, $C_2$-$C_6$-alkenyl, $C_2$-$C_6$-alkynyl, $C_1$-$C_6$-alkoxy or $C_3$-$C_8$-cycloalkyl, wherein the radicals may be unsubstituted, partially or fully halogenated.

6. The Indanyl- or Tetrahydronaphthyl-amino-azoline compound of formula I according to claim 1, wherein m is 3 and R$^2$ is substituted at positions A, C and D.

7. The Indanyl- or Tetrahydronaphthyl-amino-azoline compound of formula I according to claim 1, wherein m is 2 and R$^2$ is substituted at positions A and C.

8. The Indanyl- or Tetrahydronaphthyl-amino-azoline compound of formula I, according to claim 1, wherein m is 2 and R$^2$ is substituted at positions C and D.

9. The Indanyl- or Tetrahydronaphthyl-amino-azoline compound of formula I according to claim 1, wherein m is 1 and R$^2$ is substituted at position A.

10. The Indanyl- or Tetrahydronaphthyl-amino-azoline compound of formula I according to claim 1, wherein m is 1 and R$^2$ is substituted at position C.

11. The Indanyl-amino-azoline compound of the formula I according to claim 1, wherein n is 1.

12. The Tetrahydronaphthyl-amino-azoline compound of the formula I according to claim 1, wherein n is 2.

13. The Indanyl- or Tetrahydronaphthyl-amino-azoline compound of formula I according to claim 1, wherein m is 2 or 1.

14. The Indanyl- or Tetrahydronaphthyl-amino-azoline compound of formula I according to claim 1, wherein X is S or O.

15. An Indanyl- or Tetrahydronaphthyl-amino-azoline compound of formula I according to claim 1, wherein X is S.

16. An agricultural or veterinary composition comprising at least one pesticidal Indanyl- or Tetrahydronaphthyl-amino-azoline compound of formula I as defined in claim 1 or the enantiomers and/or at least one agriculturally useful salt thereof and at least one inert liquid and/or solid agronomically acceptable carrier and, optionally, at least one surfactant.

17. A method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of at least one Indanyl- or Tetrahydronaphthyl-amino-azoline compound of formula I as defined claim 1 or the enantiomers or at least one agriculturally or veterinary acceptable salt thereof.

18. A method for protecting crops from attack or infestation by animal pests, which comprises contacting a crop with a pesticidally effective amount of at least one Indanyl- or Tetrahydronaphthyl-amino-azoline compound of formula I as defined in claim 1 or the enantiomers or at least one agricultural acceptable salt thereof.

19. The method as defined in claim 17, wherein the animal pests are insects, arachnids or nematodes.

20. The method as defined in claim 18, wherein the animal pests are insects, arachnids or nematodes.

21. The method as defined in claim 17, wherein the animal pest are insects like *Homoptera, Lepidoptera* or *Coleoptera* or arachnids of the order of Acarina.

22. The method as defined in claim 18, wherein the animal pest are insects like *Homoptera, Lepidoptera* or *Coleoptera* or arachnids of the order of Acarina.

23. A method for the protection of seeds from soil insects and of the seedlings' roots and shoots from insects comprising contacting the seeds before sowing and/or after pregermination with an Indanyl- or Tetrahydronaphthyl-amino-azoline compound of formula I as defined in claim 1 or the enantiomers and/or at least one agriculturally acceptable salt thereof, in pesticidally effective amounts.

24. The method according claim to 23, wherein the Indanyl- or Tetrahydronaphthyl-amino-azoline compound is applied in an amount of from 0.1 g to 10 kg per 100 kg of seeds.

25. A method according to claim 23, wherein of the resulting plant's roots and shoots are protected.

26. A method according to claim 23, wherein the resulting plant's shoots are protected from aphids.

27. Seed comprising an Indanyl- or Tetrahydronaphthyl-amino-azoline compound of the formula I as defined in claim 1 or the enantiomers and/or an agriculturally acceptable salt thereof in an amount of from 0.1 g to 10 kg per 100 kg of seed.

28. A method for treating, controlling, preventing or protecting animals against infestation or infection by parasites which comprises orally, topically or parenterally administering or applying to the animals a parasiticidally effective amount of an Indanyl- or Tetrahydronaphthyl-amino-azoline compound of formula I as defined in claim 1 or the enantiomers and/or an veterinary acceptable salt thereof.

* * * * *